(12) United States Patent
Abduljauwad et al.

(10) Patent No.: US 12,076,415 B2
(45) Date of Patent: Sep. 3, 2024

(54) USE OF NANO-SIZED CLAY CRYSTALLITES TO RESTORE ADHESION AMONG TUMOR AND AGING STEM CELLS

(71) Applicant: King Fahd University of Petroleum and Minerals, Dhahran (SA)

(72) Inventors: Sahel Nishat Abduljauwad, Dhahran (SA); Habib-ur-Rehman Ahmed, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 235 days.

(21) Appl. No.: 15/877,601

(22) Filed: Jan. 23, 2018

(65) Prior Publication Data

US 2019/0054185 A1    Feb. 21, 2019

Related U.S. Application Data

(60) Provisional application No. 62/547,386, filed on Aug. 18, 2017.

(51) Int. Cl.
| | |
|---|---|
| *C01B 33/38* | (2006.01) |
| *A61K 9/51* | (2006.01) |
| *A61K 33/26* | (2006.01) |
| *A61K 35/02* | (2015.01) |
| *A61K 35/28* | (2015.01) |
| *A61K 47/02* | (2006.01) |
| *A61K 47/69* | (2017.01) |
| *A61P 35/04* | (2006.01) |

(52) U.S. Cl.
CPC ........ *A61K 47/6923* (2017.08); *A61K 9/5115* (2013.01); *A61K 33/26* (2013.01); *A61K 35/02* (2013.01); *A61K 47/02* (2013.01); *A61P 35/04* (2018.01); *C01B 33/38* (2013.01); *A61K 35/28* (2013.01)

(58) Field of Classification Search
CPC .. A61K 47/6923; A61K 9/5115; A61K 35/02; A61K 33/26; A61K 47/02; A61K 35/28; A61K 2300/00; A61P 35/04; C01B 33/38
USPC ................................................. 435/325, 375
See application file for complete search history.

(56) References Cited

U.S. PATENT DOCUMENTS

| | | | |
|---|---|---|---|
| 6,146,824 A | 11/2000 | Bar-Shavit | |
| 2006/0193787 A1* | 8/2006 | Feng | A61K 9/167 424/46 |
| 2013/0101645 A1* | 4/2013 | Scruggs | A61K 33/12 424/683 |
| 2014/0350145 A1 | 11/2014 | Smith et al. | |
| 2020/0230051 A1* | 7/2020 | Lichter | A61K 38/1825 |

FOREIGN PATENT DOCUMENTS

| | | | |
|---|---|---|---|
| JP | 2013-102713 | 5/2013 | |
| JP | 5880181 | 3/2016 | |
| WO | WO-03059263 A2 * | 7/2003 | A61K 31/74 |
| WO | WO-2007051427 A1 * | 5/2007 | A61K 33/12 |
| WO | WO 2008/039530 A2 | 4/2008 | |
| WO | WO-2017072755 A1 * | 5/2017 | A61L 24/0015 |

OTHER PUBLICATIONS

Popryadukhin et al. Cell and Tissue Biology, 2012, vol. 6, No. 1, pp. 82-88. (Year: 2012).*
Ahmed et al. Am J Stem Cells 2016;5(4):107-115 (Year: 2016).*
Zychowski et al. Mitigation of Colitis with NovaSil Clay Therapy, Dig Dis Sci (2015) 60:382-392. (Year: 2015).*
Rosenblum (2018) Nature Communications: 9:1410, pp. 1-12 (Year: 2018).*
F.B. Barlas, et al., "Folic acid modified clay/polymer nanocomposites for selective cell adhesion", Journal of Materials Chemistry B, Issue 37, Jul. 23, 2014, pp. 6412-6421.
Si-Shen Feng, et al., "Poly(lactide)-vitamin E derivative/ montmorillonite nanoparticle formulations for the oral delivery of Docetaxel", Biomaterials, vol. 30, Issue 19, Jul. 2009, pp. 3297-3306.
Nicolo Mauro, et al., "RGD-mimic polyamidoamine-montmorillonite composites with tunable stiffness as scaffolds for bone tissue-engineering applications", Journal of Tissue Engineering and Regenerative Medicine, vol. 11, Issue 7, Jul. 2017, pp. 2164-2175.
Yali Zeng, et al., "Assessment of genetic toxicity with major inhalable mineral granules in $A_{549}$ cells", Applied Clay Science, vol. 119, Part 1, Jan. 2016, pp. 175-182.
Dinesh R. Katti, et al., "Molecular interations in biomineralized hydroxyaptite amino acid modified nanoclay: In silico design of bone biomaterials", Materials Science and Engineering C, Oct. 5, 2014.

* cited by examiner

*Primary Examiner* — Janet L Epps-Smith
(74) *Attorney, Agent, or Firm* — Oblon, McClelland, Maier & Neustadt, L.L.P.

(57) ABSTRACT

A method for enhancing or restoring adhesion to cells that have partially or completely loss the ability to adhere to a substrate or other cells using nanosized clay crystallites.

4 Claims, 14 Drawing Sheets

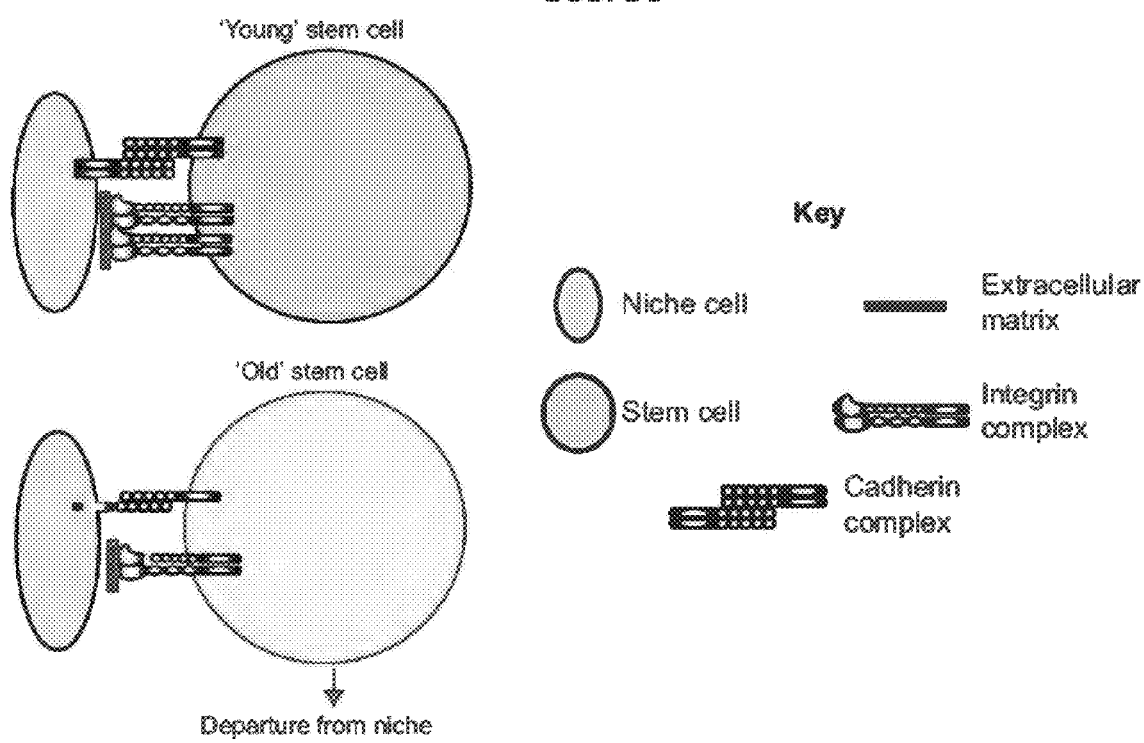

300 Angstroms

Trial 1

Trial 2

Trial 3

Raji-fibronectin interaction (Trial 1)

Raji-fibronectin interaction (Trial 2)

Raji-fibronectin interaction (Trial 3)

MSC-fibronectin interaction (Trial1)

MSC-fibronectin interaction (Trial 2)

MSC-fibronectin interaction (Trial 3)

USE OF NANO-SIZED CLAY CRYSTALLITES TO RESTORE ADHESION AMONG TUMOR AND AGING STEM CELLS

CROSS-REFERENCE TO RELATED APPLICATION

This application claims priority to U.S. Provisional Application No. 62/547,386, filed Aug. 18, 2017 which is incorporated by reference in its entirety.

STATEMENT REGARDING PRIOR DISCLOSURES BY THE INVENTOR(S)

Aspects of this technology are described by Ahmed, et al., Am. J. Stem Cells (2016) 5(4):1007-115.

BACKGROUND

Field of the Invention

A method for enhancing or restoring adhesion to cells that have partially or completely loss the ability to adhere to other cells or to a substrate using nanosized clay crystallites.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

The integrity of the human tissues is promoted through the cell-to-cell and cell-to-extracellular matrix (ECM) adhesions. Cell-to-cell adhesions are mediated through adhesion molecules in the cadherin family while cell-to-ECM adhesions are promoted through various receptors including syndecans, dystroglycan, and integrins; see Danen E H. *Integrin Signaling as a Cancer Drug Target*. Cell Biol 2013; 135164: 1-14. Classical cadherin molecules mediate cell-to-cell adhesion via homophilic interactions between the extracellular domains of cadherins on adjacent cells and via interactions of cadherin intracellular domains with cytoskeleton-associated proteins; see Chen S, Lewallen M and Xie T. *Adhesion in the stem cell niche: biological roles and regulation*. Development 2013; 140: 255-265. Integrins are heterodimeric transmembrane molecules that mediate cell-ECM interactions and contain α and β subunits; see Chen S, Lewallen M and Xie T. *Adhesion in the stem cell niche: biological roles and regulation*. Development 2013; 140: 255-265. The extracellular domains of integrins can bind directly to ECM proteins such as laminin, collagen, and fibronectin; see Barczyk M, Carracedo S and Gullberg D. Integrins. Cell Tissue Res 2010; 339: 269-280; Hynes R O. *Integrins: bidirectional, allosteric signaling machines*. Cell 2002; 110: 673-687. In addition to ECM components, integrins can also bind to other cell-surface adhesion molecules such as intercellular adhesion molecule 1 (ICAM 1, also known as CD54) and vascular cell adhesion molecule 1 (VCAM 1, also known as CD106). These cell adhesion molecules are known to be present in some stem cell niches; Barczyk M, Carracedo S and Gullberg D. *Integrins*. Cell Tissue Res 2010; 339: 269-280.

A relationship of focal adhesions ("FA") and cancer cell migrations is described by Nagano M, Hoshino D, Koshikawa N, Akizawa T and Seiki M. *Turnover of Focal Adhesions and Cancer Cell Migration*. Int J Cell Biol 2012; 2012: 310616 who studied the cell adhesion to the ECM and determined the turnover of FAs using cells cultured on an ECM-coated substratum. It was discovered that adhesion of cells to the ECM is key to regulation of cellular morphology, migration, proliferation, survival, and differentiation; see Gumbiner B M. *Cell adhesion: the molecular basis of tissue architecture and morphogenesis*. Cell 1996; 84: 345-357; Hynes R O and Lander A D. *Contact and adhesive specificities in the associations, migrations, and targeting of cells and axons*. Cell 1992; 68: 303-322. Numerous proteins are involved in integrin-mediated cell adhesion and these proteins are collectively referred to as the "adhesome"; Whittaker C A, Bergeron K F, Whittle J, Brandhorst B P, Burke R D and Hynes R O. *The echinoderm adhesome*. Dev Biol 2006; 300: 252-266. Among the latter, talin is a key regulator of an initial step of FA assembly. The binding of talin to integrin stabilizes the ligand-induced clustering of the latter at an initial stage of FA formation by mediating crosslinking of integrins with filamentous actin ("F-actin") and F-actin-binding proteins such as vinculin and α-actinin; see FIG. 1A.

Both α- and β-subunits of integrins are type I transmembrane proteins and contain both a large extracellular domain responsible for binding to ECM ligands and a cytoplasmic portion (CP) that recruits multiple intracellular proteins. Each integrin recognizes a distinct ECM ligand and the common integrin binding motif, Arg-Gly-Asp (RGD), is shared by several ECM proteins, including fibronectin, vitronectin, and fibrinogen. Integrin binding to laminins and collagens occurs at other recognition motifs; see Danen E H. *Integrin Signaling as a Cancer Drug Target*. Cell Biol 2013; 135164: 1-14.

The decrease in or loss of cells' mutual adhesiveness has been considered as one of the specific abnormalities in the surface properties of malignant cells. A change in the association of plasma membrane with cytoskeletal structures also seems to have a close relation with these abnormalities.

Similar to the role of adhesions in tumor cells, stem cells' self-renewal is also tightly controlled. FIG. 1A depicts a schematic representation of the formation and FIG. 1B the turnover of focal adhesions in the cell to extracellular matrix (ECM). FIG. 1C is a representation of the expression levels or functions of adhesion molecules in stem cells and niche cells are affected by aging by the concerted action of stem cell-intrinsic factors and signals within the niche; see Chen S, Lewallen M and Xie T. *Adhesion in the stem cell niche: biological roles and regulation*. Development 2013; 140: 255-265. FIGS. 1A, 1B and 1C were taken from Nagano M, Hoshino D, Koshikawa N, Akizawa T and Seiki M. *Turnover of Focal Adhesions and Cancer Cell Migration*. Int J Cell Biol 2012; 2012: 310616 which is incorporated by reference.

Niche signals often function within a short range allowing cells in the niche to self-renew while their daughters outside the niche differentiate. Thus, for stem cells to continuously self-renew they are often anchored in the niche via adhesion molecules. In addition to niche anchoring, however, recent studies have revealed other important roles for adhesion molecules in the regulation of stem cell function and it is clear that stem cell niche adhesion is crucial for stem cell self-renewal and is dynamically regulated.

The loss of adhesion is a hallmark of both tumor and aging stem cells. This loss results in migration of the tumor cells to other parts of the body where the produce metastases and is known as metastatic cancer. Most cancer patient mortality occurs due to metastatic cancers. Besides the role of loss of adhesion in metastatic cancer, there are several other consequences of loss of adhesion including lack of communication.

Restoration of tumor cell adhesions, therefore, may control the tumor cells' migration resulting in the formation of metastatic cancers may restore the cell communication. Moreover, restoration of stem to niche cell adhesions may restore the differentiation ability of the divided aged stem cells resulting in the formation of new tissues.

As disclosed by the inventors herein, the restoration of adhesions among tumor or stem cells may be accomplished by use of inorganic nanosized clay crystallites. Among clay minerals, smectite carries electrostatically charged particles. The charge deficiency in smectite clay, occurring due to isomorphous substitution in their molecular structure, is balanced by cations sorbed on their surfaces. Due to the charged structure, smectite clay particles have an affinity for other charged substances such as bacteria and the toxins. Due to this property smectite clays have been used as alternative medicine for several ailments; see Guo M Y, Wang A F, Muhammad F, Qi W X, Ren H, Guo Y J and Zhu G S. Halloysite *Nanotubes, a Multifunctional Nanovehicle for Anticancer Drug Delivery*. Chinese Journal of Chemistry 2012; 30: 2115-2120; Martinez C D. *Cationic Clays upon Cancer Therapy*. Virtual Multidisciplinary Conference QUAESTI 2013; 16-20; Konta J. *Clay and man: Clay raw materials in the service of man*. Appl Clay Sci 1995; 10: 275-335; Murray H H. *Traditional and new applications for kaolin, smectite, and palygorskite: a general overview*. Appl Clay Sci 2000; 17: 207-221; Volzone C. *Retention of pollutant gases: Comparison between clay minerals and their modified products*. Appl Clay Sci 2007; 36: 191-196; Lin F H, Lee Y H, Jian C H, Wong J M, Shieh M J and Wang C Y. *A study of purified montmorillonite intercalated with 5-fluorouracil as drug carrier*. Biomaterials 2002; 23: 1981-1987; and Dong Y and Feng S S. *Poly(d,l-lactide-coglycolide)/montmorillonite nanoparticles for oral delivery of anticancer drugs*. Biomaterials 2005; 26: 6068-6076.

Besides the medical uses of smectite clays, a few studies have used clay nanoparticles as a medicine carrier; see Koutsouki E., *Mixing stem cells with clay to regenerate-human tissue* at http://_www.southampton.ac.uk/news/2014/05/01, page#.U5bof7cU-95; and Verma D, Katti K S and Katti D R. *Polyelectrolyte-Complex Nanostructured Fibrous Scaffolds for Tissue Engineering*. Materials Science and Engineering C 2009; 29: 2079-2084. Also the use of clay nanoparticles as scaffolds during the regrowth of the bone structure has been explored; see Katti D R, Sharma A, Ambre A H and Katti K S. *Molecular Interactions in Biomineralized Hydroxyapatite Between Amino Acid Modified Nanoclay: Insilico Design of Bone Biomaterials*. Mater Sci Eng C Mater Biol Appl 2015; 46: 207-217; and Ambre A H, Katti D R and Katti K S. *Nanoclays mediate stem cell differentiation and mineralized ECM formation on biopolymer scaffolds*. J Biomed Mater Res A 2013; 101: 2644-60. A simulation-driven approach was employed to demonstrate the use of nanoclays modified with amino acid to mineralize hydroxyapatite that mimics the biomineralization process. However, there is an significant absence of work directed to use of clay nanoparticles as adhesion restoring agents among cancer and stem cells.

The inventors recognized that adhesion of cells to the ECM is a key to the regulation of cellular morphology, migration, proliferation, survival, and differentiation and considered that the decrease in or loss of the cell's ability of mutual adhesiveness as one of the specific abnormalities in the surface properties of malignant cells or aged stem cells. They also considered that a change in the association of plasma membrane with cytoskeletal structures would have a close relation with these abnormalities as well as with a stem cells' capacity for self-renewal that could be tightly controlled by the concerted action of stem cell-intrinsic factors and signals within the niche.

In view of the need for a method for restoring adhesion among cancer cells and aged stem cells, the inventors sought to investigate the use of the smectite clay minerals as a therapeutic approach to preventing cancer cell migration and to modulate differentiation of stem cells. These processes have now been investigated at the molecular level by studying the interactions of the clay crystallites in environments involving cell-cell and cell-ECM adhesion using Monte Carlo (MC) and molecular dynamics (MD) simulation techniques and substantiated by experimental results obtained in the laboratory.

BRIEF SUMMARY OF THE INVENTION

In a prominent embodiment, the invention is directed to a method for restoring or enhancing adhesiveness of tumor, cancer, neoplastic and other cells that lack or have lost their adhesiveness to ECM, cells, and other substrates by contacting cells or their binding substrates with nanosized smectite. The restoration of adhesiveness provides a way to control metastasis of cancer, neoplastic, or tumor cells as well as providing a method for self-renewal of aged stem cells.

BRIEF DESCRIPTION OF THE DRAWINGS

FIGS. 1A and 1B from Nagano M, Hoshino D, Koshikawa N, Akizawa T and Seiki M. Turnover of Focal Adhesions and Cancer Cell Migration. Int J Cell Biol 2012; 2012: 310616.

FIG. 1C. Representation of the expression levels or functions of adhesion molecules in stem cells and niche cells affected by aging from Chen S, Lewallen M and Xie T. Adhesion in the stem cell niche: biological roles and regulation. Development 2013; 140: 255-265.

DETAILED DESCRIPTION OF THE INVENTION

Figure 1A:
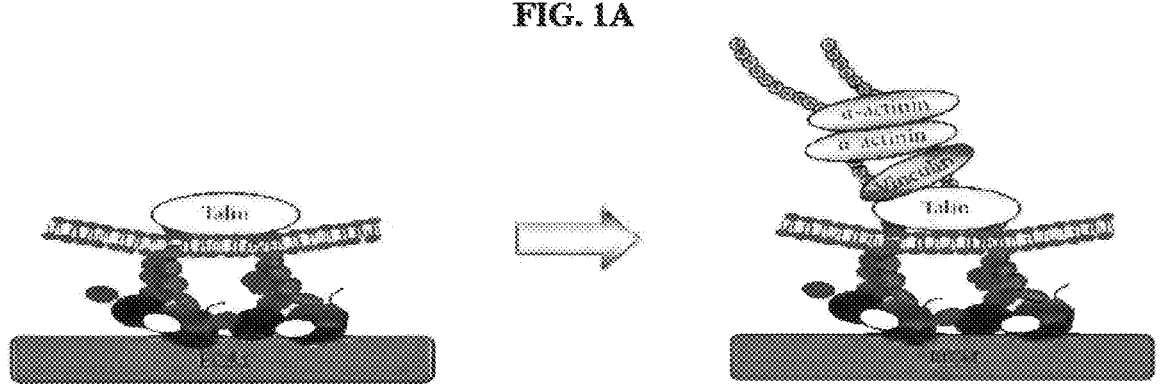
FIG. 1A. Schematic representation of the formation of focal adhesions in the cell to extracellular matrix (ECM).
Figure 1B:
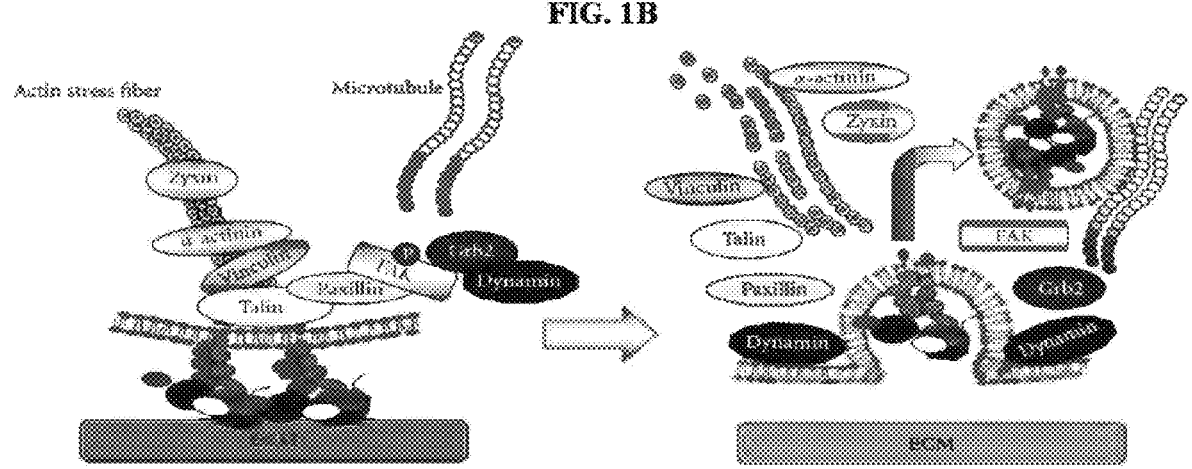
FIG. 1B. Turnover of focal adhesions in the cell to extracellular matrix (ECM).

Clays include kaolinites such as boalinite, anauxite, dickite and nacrite, montmorillonites such as montmorillonite, bentonite, bordellite and montronite, illites/muscovites such as illite and glauconite, chlorites, polygorshites such as attapulgite, halloysite, metabolloysite, allophane and aluminum silicate clays. Metal oxides such as magnesium oxide, zinc oxide, and titanium oxide may be employed to increase cohesiveness of a clay. Preferred clays for use in the invention are smectite clays.

Smectite is the name used for a group of phyllosilicate mineral species, such as montmorillonite, beidellite, nontronite, saponite and hectorite. These and several other less common species are differentiated by variations in chemical composition involving substitutions of Al for Si in tetrahedral cation sites and Al, Fe, Mg and Li in octahedral cation sites. Smectite clays have a variable net negative charge, which is balanced by Na, Ca, Mg and/or H adsorbed externally on interlamellar surfaces. The structure, chemical composition, exchangeable ion type and small crystal size of smectite clays are responsible for several unique properties, including a large chemically active surface area, a high cation exchange capacity, interlamellar surfaces having unusual hydration characteristics, and sometimes the ability to modify strongly the flow behavior of liquids. Natural smectite clays are sometimes divided into three categories, Na smectites, Ca—Mg smectites and Fuller's or acid earths.

Montmorillonite is a subclass of smectite, a 2:1 phyllosilicate mineral characterized as having greater than 50% octahedral charge; its cation exchange capacity is due to isomorphous substitution of Mg for Al in the central alumina plane. The substitution of lower valence cations in such instances leaves the nearby oxygen atoms with a net negative charge that can attract cations.

Cation exchange capacity ("CEC") is the total capacity of a material, such as a clay or soil, to hold exchangeable cations and is a measure of how many cations can be retained on clay or soil particle surfaces. Different clays or crystallites, such as various Na-montmorillonites, can have various cation exchange capacities, for example, different Na-montmorillonite molecules having three different CECs of 54, 90 and 144 meq/100 g are exemplified herein. The CEC of a clay or smectite of the invention may be classified as low CEC ("LCEC"), mid-CEC ("MCEC'), or high-CEC ("HCEC"). A CEC for a smectite or other clay of the invention may range from 40 to 240, for example, 40, 50, 60, 70, 80, 90, 100, 110, 120, 130, 140, 150, 160, 170, 180, 190, 200, 210, 220, or 240 meq/100 g. As shown herein, a smectite of clay having CEC of at least 140 meq/100 g may preferably be used. Based on the general range of CEC values for Na-montmonrillonite clay mineral, CEC numbers may be generally classified as low, medium or high.

Target cell. A target cell according to the invention is a cell that benefits from contact with smectite or other clay nanoparticles, for example, to modulate its adhesive properties to other cells or to the ECM. Generally, the cell will be one in need of increased adhesion to other cells (or cellular components such as determinants of membrane proteins or carbohydrates) or to a substrate, such as ECM, an ECM component, or an artificial substrate. Advantageously the cell will be one that has lost, is losing, or is at risk of losing is ability to adhere, such as a cancer, tumor, or neoplastic cell or an out-of-niche stem cell such as a partially differentiated or aged stem cell. An increase in adhesion encompasses an increase in the affinity or strength of binding between two or more cells or an increase in the number of points or areas of adhesion.

Target substrate. A target substrate according to the invention is a material to which a smectite or other clay nanoparticle can attach to or otherwise interact with, for example, to induce or enhance adhesion of a cell to the substrate. It includes ECM, bone, cellular or ECM components, and artificial substrates.

Metastatic tumor or cancer cells. Metastatic cancer has the same name and the same type of cancer cells as the original, or primary, cancer. For example, breast cancer that spreads to the lung and forms a metastatic tumor is metastatic breast cancer, not lung cancer. In contrast, cancer in situ or in situ cancer refers to an early stage cancer in which the cancerous growth or tumor is still confined to the site from which it started and has not spread to surrounding tissue or other organs in the body. For example, cancer in situ involves cells that line the internal organs or epithelial cells that has not metastasized. The method of the invention is advantageously used to treat cancer in situ, but can also be used to treat cancer at sites of metastasis in order to prevent, treat, or inhibit further metastasis.

Cancer cells spread through the body in a series of steps. These steps include (i) growing into, or invading, nearby normal tissue, (ii) moving through the walls of nearby lymph nodes or blood vessels, (iii) traveling through the lymphatic system and bloodstream to other parts of the body, (iv) stopping in small blood vessels at a distant location, invading the blood vessel walls, and moving into the surrounding tissue, (v) growing in this tissue until a tiny tumor forms, and (vi) causing new blood vessels to grow, which creates a blood supply that allows the tumor to continue growing. Some common cancer types and their main sites of metastasis are described below. These associations aid in selection of a site or mode of administration of the nanoparticles according to the invention.

| Cancer Type | Main sites of metastasis |
| --- | --- |
| Bladder | Bone, liver, lung |
| Breast | Bone, brain, liver, lung |
| Colon | Liver, lung, peritoneum |
| Kidney | Adrenal gland, bone, brain, liver, lung |
| Lung | Adrenal gland, bone, brain, liver, other lung |
| Melanoma | Bone, brain, liver, lung, skin, muscle |
| Ovary | Liver, lung, peritoneum |
| Pancreas | Liver, lung, peritoneum |
| Prostate | Adrenal gland, bone, liver, lung |
| Rectal | Liver, lung, peritoneum |
| Stomach | Liver, lung, peritoneum |
| Thyroid | Bone, liver, lung |
| Uterus | Bone, liver, lung, peritoneum, vagina |

In some embodiments of the invention, the site of the initial cancer is treated with a smectite to increase the adhesiveness of the cancer or tumor cells and prevent metastasis. For example, colon cancer may be treated with a smectite to prevent its metastasis to nearby tissue, vascular tissue, lymph nodes or more distant metastasis to the liver, lung, or peritoneum. In some embodiments, cancer or tumor cells associated with bone may be treated, in others the cancer or tumor will not be associated with bone. Similarly, stem cells, such as aged or partially differentiated stem cells, may be used to treat or produce bone tissue, but in other embodiments, they are used to treat or produce non-bone tissues.

Stem cells are undifferentiated biological cells that can differentiate into specialized cells and can divide through mitosis to produce more stem cells. They are found in multicellular organisms. In mammals, there are two broad types of stem cells: embryonic stem cells, which are isolated from the inner cell mass of blastocysts, and adult stem cells, which are found in various tissues. Stem cells may be isolated from bone marrow, adipose tissue (lipid cells), or blood, including from umbilical cord blood. In some embodiments, cultured or artificially grown, aged, or partially differentiated stem cells may be used. In other embodiments, the stem cells may be isolated from an individual. Two mechanisms exist which maintain stem cell population: obligatory asymmetric replication in which a stem cell divides into one mother cell that is identical to the original stem cell and another daughter cell that is differentiated; and stochastic differentiation in which one stem cell develops into two differentiated daughter cells, another stem cell undergoes mitosis and produces two stem cells identical to the original. Stem cells include totipotent stem cells can differentiate into embryonic and extraembryonic cell types; pluripotent stem cells are the descendants of totipotent cells and can differentiate into nearly all cells, i.e. cells derived from any of the three germ layers; multipotent stem cells can differentiate into a number of cell types, but only those of a closely related family of cells; oligopotent stem cells can differentiate into only a few cell types, such as lymphoid or myeloid stem cells; and unipotent cells that can produce only one cell type, their own, but have the property of self-renewal, which distinguishes them from non-stem cells (e.g, from progenitor cells, which cannot self-renew). The nanoparticles of the invention may be used to enhance adhesion between different kinds of stem cells (for example, stem cells in different niches) and reverse differentiation or enhance self-renewing properties of stem cells.

Different kinds or sources of stem cells may be used in various embodiments of the invention. In some embodiments, stem cells to be administered into or contacted with bone (e.g., to promote regrowth, fusion, or treat osteoporosis) may be treated with the nanoparticles disclosed herein, in others the stem cells will be administered or contacted with tissues other than bone. In many embodiments, the compositions containing the nanoparticles of the invention will actively interact with tumor or cancer cells or actively participate in tissue regeneration induced in aged, partially differentiated, or other stem cells rather than be limited to mere scaffold support or use as excipients for other active ingredients.

Nanoparticles or nanosized particles refer to particles having a mean particle size ranging from 1 nm to <1,000 nm, which range includes all intermediate values and subranges, such as 1, 2, 5, 10, 15, 20, 25, 30, 35, 40, 45, 50, 60, 70, 75, 100, 150, 200, 250, 300, 350, 400, 450, 500, 550, 600, 650, 700, 750, 800, 850, 900, 950, and <1,000 nm, for example, as determined using transmission electron microscopy ("TEM"). Nanoparticles according to the invention may have a mean diameter of less than 5, 10, 15, 20 or 25 nm. Crystallites may have an irregular structure such as that described in the Example below: 26×108×20 Å (2.6×10.8× 2.0 nm). Based on particle size analysis of several clays described below using Dynamic Light Scattering (DLS) technique, the mean and maximum particle sizes may be advantageously selected within ranges of 1, 2, 5, 10, 20, or 50% smaller or larger (or any intermediate subrange or value) to the mean or maximum sizes described below:

| Clay mineral | Mean size (nm) | Maximum size (nm) |
| --- | --- | --- |
| Palygorskite | 30 | 75 |
| Hectorite | 50 | 100 |
| Na-montmorillonite | 55 | 100 |

Nanoparticle dimensionality may fall within 1, 2, 5, 10, 20 or 50% smaller or larger (or any intermediate subrange or value) than the dimensions described below.

| Clay mineral | Mean size from DLS (nm) | Size/dimensions range (nm) |
| --- | --- | --- |
| Palygorskite | 27.6 | 27.6 × 2.6 × 2.6 |
| Hectorite | 50.1 | 50.1 × 5.0 × 20 |
| Na-montmorillonite | 54.5 | 50.1 × 50.1 × 2.0 |

Nanoparticles may be prepared in an aggregated form or non-aggregated form, for example, by sonication or adjustment of surface charge. In some embodiments the agglomeration or aggregation of nanoparticles (e.g., to keep them in a colloidal suspension) may be inhibited by coating them with various polymers like polyethylene glycol (PEG) or poly(vinylpyrrolidone) (PVP), natural polymers like dextran, chitosan, or pullulan, or with surfactants like sodium oleate or dodecylamine.

Nanoparticles according to the invention may be targeted to a specific anatomical location, a specific organ, a specific tissue, a specific site in an organ or tissue (such as a neoplastic lesion), or a specific component of a substrate or cell. By adjustment of size, charge and surface characteristics they may be targeted to the outside or inside of a cell.

Advantageously different nanoparticles may be used for similar or different cellular or ECM configurations, such as those described below.

| Clay mineral type | Shape | Suitable for configuration |
|---|---|---|
| Palygorskite | Elongated | Cancer cell-ECM |
| Hectorite | Platy-elongated | Cancer cell-ECM, Stem cells |
| Na-montmorillonite | Equidimensional | Cancer cells |

Other active ingredients. In most embodiments, the clay minerals used in the compositions of the invention are non-toxic and lack cytotoxicity toward normal and stem cells as well as lack environmental toxicity. However, in some embodiments where induced cytotoxicity may occur such as in the presence of other active anticancer agents, the smectite or clay nanoparticles may be administered along with an antioxidant (e.g., an antioxidant enzyme such as superoxide dismutase, catalase, glutathione peroxidase, glutathione S-transferase or glutathione reductase; melatonin; an antioxidant nutrient such as vitamin A, C or E, lipoic acid, cysteine, acetylcysteine, etc; or a chemical antioxidant such as DTT or 2-beta mercaptoethanol) to reduce oxidative stress; an anti-inflammatory drug to reduce inflammation associated with the administration of nanoparticles (e.g., an NSAID such as aspirin, ibuprofen, or naproxen; an antileukotrine, an ImSAID, bromelain or other plant-based anti-inflammatory, or cannabichromene or another anti-inflammatory cannaboid); or with a drug that inhibits cytokine activity associated with the administration of the nanoparticles, such as OX40 IG, ACE inhibitors, Angiotensin II receptor blockers, corticosteroids, Gemfibrozil, free radical scavengers, or TNF-alpha blockers.

In other embodiments, clay or smectite nanoparticles may be administered in conjunction with treatment with one or more anti-cancer agents, including surgical resection, radiation, immunotherapy, targeted cytotoxic treatment, or chemotherapy.

Functionalization. In some embodiments, nanoparticles according to the invention may be functionalized by covalent or noncovalent bonding to a targeting or detection tag moiety, such as an antibody that binds to a cellular antigen or tumor-associated antigen or epitope, a ligand for a cell surface molecule or receptor, or a nucleic acid such as a probe or vector, a label or marker such as a fluorescent marker like GFP or luminescent marker such as luciferin, a drug, a radioactive material, or polymer or lipid material such as one that can modify surface features of the nanoparticles.

Pharmaceutical compositions. A pharmaceutical composition containing nanosized clay or smectite will generally contain a sufficient amount of the smectite or clay nanoparticles to increase cellular adhesion when contacted with a target cell such as a tumor or cancer cell which is losing or has lost its ability to adhere. Smectite- or clay-containing compositions may be prepared in or as solutions, serums, lotions, creams, pastes, ointment/salves, gels, aerosols, foams and other conventional formulations using known excipients or carriers.

Solutions. While any suitable liquid carrier known to those of ordinary skill in the art may be employed in a pharmaceutical solution or suspension containing the nanoparticles according to the invention, the type of liquid carrier will vary depending on the mode of administration. For parenteral administration, such as subcutaneous, intramuscular, or intravenous injection, the carrier preferably comprises water, saline (such as normal saline), an aqueous solute containing another salt such as a sodium, potassium, magnesium, or calcium halogen or phosphorous-containing salt, $C_1$-$C_5$ alcohol, a sugar or sugar alcohol, a fat, a wax, a buffer, or acid or base.

Encapsulation. The smectite or other clay nanoparticles described herein can be encapsulated in a carrier such as in liposomes, micelles, or microspheres. Suitable carriers are described in U.S. Pat. No. 7,205,003, hereby incorporated by reference.

Micelles provided herein can comprise surfactant molecules arranged such that their polar head groups form an outer spherical shell, while their hydrophobic, hydrocarbon chains are oriented towards the center of the sphere, forming a core. The precursor and smectite or other clay are encapsulated within the core of the micelle. Surfactants suitable for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethyl-ammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Liposomes are microscopic vesicles having a lipid wall comprising a lipid bilayer which may be formulated to carry or contain a smectite or other clay nanoparticle. Liposomal preparations herein include cationic (positively charged), anionic (negatively charged), and neutral preparations including the smectite or other clay. Cationic liposomes include N[1-2,3-dioleyloxy)propyl]-N,N,N-triethylammonium (DOTMA). Anionic and neutral liposomes can be easily prepared using materials such as phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE). These materials can also be mixed with DOTMA in appropriate ratios.

Microspheres provided herein can comprise micro- or nano-scale carriers that are made of polymers, both synthetic and natural and which contain the smectite or clay nanoparticles. Microspheres include, but are not limited to, spheres, beads, particles, carriers, microbeads, microparticles, microcarriers, nanospheres, nanobeads, nanoparticles, and nanocarriers. Polymeric materials suitable for producing microspheres include those that are described in U.S. Pat. No. 6,423,345, hereby incorporated by reference in its entirety, including poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. Polymer derivatives, such as polymers having substitutions, additions of chemical groups, for example, alkyl, alkylene, hydroxylations, oxidations, and other modifications routinely made by those skilled in the art may be used. Natural polymers including agarose and alginate are also suitable for the microspheres. Smectite or clay nanoparticles can be encapsulated using known techniques in the art, such as those described in U.S. Pat. No. 6,423,345, incorporated by reference. These include solvent evaporation, hot melt microencapsulation, solvent removal, and spray drying of microspheres.

Sustained-release formulations may be prepared. Examples of sustained-release preparations include semipermeable matrices of solid hydrophobic polymers containing the smectite or clay nanoparticles that release the nanoparticles over a period of time. The matrices may be in the form of shaped articles including films or microcapsules. Examples of sustained-release matrices include polyesters, hydrogels, for example, poly(2-hydroxyethyl-methacrylate), or poly(vinylalcohol), polylactides, copolymers of L-glutamic acid and ethyl-L-glutamate, non-degradable ethylene-vinyl acetate, and degradable lactic acid-glycolic acid copolymers such as the LUPRON DEPOT™ which are injectable microspheres composed of lactic acid-glycolic acid copolymer and leuprolide acetate. Sustained release compositions useful herein may be adapted for immediate, delayed, modified, sustained, pulsed or controlled release of a compound of the invention. For example, a clay or smectite nanoparticle composition may be formulated to release the active compounds over a period of 1, 2, 3, 4, 5, 6, 7, 8, 9, 10, 12, 18, 20 or 24 hours or 1, 2, 3, 4, 6, 8, 10, 12 or 14 days. These ranges include all intermediate subranges and values.

Suppositories. In addition to the active clay or smectite nanoparticles, a suppository may contain the customary water-soluble or water-insoluble excipients, for example polyethylene glycols, fats, for example cocoa fat and higher esters (e.g., $C_{14}$-alcohol with $C_{16}$-fatty acid) or mixtures of these substances.

Tablets, Capsules, Pills. In some embodiments, a smectite or clay may be formulated as a tablet, capsule or pill, for example, to target the nanoparticles to gastric or intestinal tissues or for absorption of the nanoparticles. These may contain the customary excipients, such as fillers and extenders, for example starches, lactose, sucrose, glucose, mannitol, and silicic acid; binders, for example carboxymethyl cellulose, alginates, gelatin, polyvinylpyrrolidone; humectants, for example glycerin; disintegrating agents, for example agar-agar, calcium carbonate and sodium carbonate; dissolution retardants, for example paraffin; resorption accelerating agents, for example quaternary ammonium compounds; wetting agents, for example cetyl alcohol, glycerol monostearate; adsorption agents, for example kaolin and bentonite; and lubricants, for example talcum, calcium stearate and magnesium stearate, and solid polyethylene glycols or mixtures of the substances mentioned above. In some embodiments, the active ingredient(s) can be in a microencapsulated form in the tablet or capsule, which can optionally be formulated to release the active clay or smectite component at a particular location within the body or over a particular period of time. Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Smectite of clay nanoparticles can also be administered in a form of a hard shell tablet or a capsule containing a binder, e.g., lactose or mannitol, a conventional filler, and a tableting agent.

Powders may be formulated to contain dry or encapsulated smectite or clay nanoparticles and a customary excipients, for example lactose, talcum, silicic acid, aluminum hydroxide, calcium silicate, and polyamide powder, or mixtures of these substances. A powder may be formulated for admixture or suspension with a pharmaceutically acceptable solution for later administration, preferably in a unit dosage.

The pH. A composition may have an acidic or basic pH, such as a pH ranging from 1, 2, 3, 4, 5, 6, 7, 8, 9, 10, 11, 12, 13 to 14 (or any intermediate value within this range), for many modes of administration preferably from 3 to 9, more preferably from 5.5 to 8.5. It may match or coordinate to the pH of the site of administration or type of nonadherent cells, or vary upward or downward by about 0.1, 0.2, 0.5, 1.0, 1.5 or 2.0 pH units from the pH of the administration or treatment site. A pH may be adjusted by the addition of an acid, such as an organic acid, or inorganic acid such as HCl, or base, such as sodium hydroxide, or by the incorporation of a buffer.

Administration. There are several methods and vehicles for administering the composition to a subject that are within the scope of the method for enhancing adhesiveness of tumor, neoplastic, cancer or other target cells that have lost or are losing adhesiveness. These methods include any therapeutically acceptable manner of administering a therapeutic material. In a preferred embodiment of the invention, the smectite or clay nanoparticle composition is administered to an anatomical site containing the target cells. The composition may be administered by in situ injection or in situ perfusion or wash. It may be administered parenterally, for example, by percutaneous, intramuscular, or intravenous injection. It may be administered topically to skin or a mucous membrane, for example, as a topical cream, gel, ointment, emulsion, suppository, and/or paste. It may be administered orally such as by incorporation into a tablet, capsule, pill, powder, liquid, drink, and/or food.

A composition containing clay or smectite nanoparticles may be administered directly, for example, directly on to a site containing the target cells or indirectly such as into blood, plasma, lymph, interstitial fluid, CSF, joint fluid or other physiological fluids. A solution or suspension containing a clay or smectite according to the invention may contain a liquid carrier suitable for suspending or emulsifying the clay or smectite. A therapeutic composition described herein may range from >0, 0.001, 0.002, 0.005, 0.01, 0.02, 0.05, 0.1, 0.2, 0.5, 1.0, 2.0, 5.0, 10.0, 20.0, 50.0 and <100 wt % of the smectite or clay nanoparticles. A suitable dosage may be determined by those skilled in the art, for example, by methods disclosed herein. Advantageously, the amount of smectite or clay nanoparticles will be no more than 20, 10, 5, 4, 3, 2, 1, 0.5, 0.2, 0.1, 0.05, 0.02 or 0.01 mg/cc.

A solution or other therapeutic composition may be formulated to contain a concentration of 0.1, 0.2, 0.5, 1.0, 2.0, 5.0 or 10.0 or more times the concentration of the smectite or clay nanoparticles required to increase adhesiveness of the target cell. However, in some embodiments a lower concentration may be used, for example, in a mixed composition containing other active ingredients that promote adhesion or when a series of repeated doses are given.

Local administration as used herein refers to modes of administration that cause the clay or smectite nanoparticles to be delivered selectively to target cells at a specific site, for example, cells of a cancer in situ or tumor in situ or to a site proximal to the site of a cancer or tumor. Depending on the type of cancer or tumor, local administration may involve parenteral injection or administration into a tumor mass, oral administration, enteral administration, administration to or into a mucous membrane, or percutaneous or topical administration to a site proximal to the target cells. Advantageously, for skin cancer, a composition of the invention may be administered topically or subcutaneously. A representative topical dosage for skin cancer is about 0.5 mg/ml and for subcutaneously administration for skin cancer about 0.2 mg/ml. These dosages may be increased or decreased based on the type, location and extent of skin cancer, for example, by decreasing or increasing the concentration of clay nanoparticles by 5, 10, 20, 50, 100, 200 or 500% (or any intermediate subrange or value) based on the concentrations described above.

Systemic administration is a route of administration of clay or smectite nanoparticles into the circulatory system so that the entire body is affected. Systemic administration can take place via enteral administration (absorption of the drug through the gastrointestinal tract) or parenteral administration (generally injection, infusion, or implantation). In some embodiments, the smectite or clay nanoparticles may be administered into the circulatory system, lymphatic system, or CSF directly and in other indirectly, such as by adsorption through the skin, mucous membrane, respiratory system, or lining of the GI tract.

Advantageously for cancer tissue in the interior of the body, administration may be into the cancer tissue in situ which includes solid primary cancer sites as well as sites to where a cancer has metastasized. Systemic administration such as intravenous administration is also preferred for circulating or non-solid cancers. A representative dosage for an in situ injection into cancer tissue is about 0.2 mg/ml and for intravenous administration for a circulating or non-solid cancer about 0.1 mg/ml. These dosages may be increased or decreased based on the type, location and extent of in situ cancer tissue or circulating or non-solid cancer, for example, by decreasing or increasing the concentration of clay nanoparticles by 5, 10, 20, 50, 100, 200 or 500% (or any intermediate subrange or value) based on the concentration described above. Intravenous administration of the clay nanoparticle composition of the invention will help capture circulating tumor cells ("CTCs") by adhering to the CTCs due to their high non-specific adhesions as compared to other blood constituents and thus inhibit their metastasis, e.g., by prevent adhesion to a site of metastasis to which the CTC could otherwise adhere or colonize.

Among many other embodiments, the invention is directed to:
1. A method for treating a cancer, neoplasm, tumor or proliferative disease, disorder or condition comprising contacting the cells with nanosized smectite for a time an in an amount sufficient to increase the adhesion of the cells to a substrate, to each other, or to other cells compared to otherwise identical cells not treated with the nanosized smectite.
2. The method of embodiment 1, wherein said cells are primary cancer, neoplasm, or tumor cells.
3. The method of embodiment 1, wherein said cells are localized to an organ or tissue containing the primary cancer, neoplasm, or tumor cells.
4. The method of embodiment 1, wherein said cells are localized to an organ or tissue containing the primary cancer, neoplasm, or tumor cells or to lymph nodes.
5. The method of embodiment 1, wherein said cells have metastasized to other parts of the body other than the organ or tissue containing the primary cancer, neoplasm, or tumor cells.
6. The method of embodiment 1, wherein the nanosized smectite comprises Na-montmorillonite crystallites.
7. The method of embodiment 1, wherein the nanosized smectite has an average diameter of no more than 5, 10, 15, 20, 25, 30, 35, 40, 45, or 50 nm.
8. The method of embodiment 1, wherein the contacting comprises exposing the cells to a concentration of no more than 1, 2, 5, 10, 15, 20 or 25 mg/ml of the smectite.
9. The method of embodiment 1, wherein the nanosized smectite has a CEC value of at least 100, 110, 120, 130, 140, 150 or 160 meq/100 g.
10. The method of embodiment 1, wherein said contacting increases the adhesion of breast, cervical, colon, prostate, or lung cancer cells to cells in the organ in which they originated.
11. The method of embodiment 1, wherein said contacting increases adhesion of the cells to extracellular matrix (ECM) in the organ in which they originated.
12. The method of embodiment 1 that is performed in vivo, ex vivo or in vitro.
13. A method for increasing adhesion of stem cells comprising contacting the cells with nanosized smectite for a time an in an amount sufficient to increase the adhesion of the cells to a substrate, to each other, or to other cells compared to otherwise identical cells not treated with the nanosized smectite.
14. The method of embodiment 13, wherein the cells are partially differentiated stem cells or aged stem cells.
15. The method of embodiment 13, wherein the adhesion of the stem cells is increased for bone.
16. The method of embodiment 13, wherein the nanosized smectite has an average diameter of no more than 5, 10, 15, 20 or 25 nm.
17. The method of embodiment 13, wherein the contacting comprises exposing the cells to a concentration of no more than 1, 2, 5, 10, 15, 20, or 25 mg/ml of the smectite.
18. A composition comprising nanosized smectite and at least one stem cell.
19. The composition of embodiment 18, wherein the nanosized smectite has an average diameter of no more than 5, 10, 15, 20, or 25 nm.
20. The composition of embodiment 19, wherein the nanosized smectite is present in a concentration of no more than 10 mg/ml.

EXAMPLES

The following examples illustrate various aspects of the present invention. They are not to be construed to limit the claims. The work shown below demonstrates through both molecular simulations and laboratory work, the usefulness of smectite (e.g., Na-montmorillonite) clay crystallites to create adhesions among tumor and stem cells. For example, the high electrostatic energies and cohesive energy densities measured in the simulations after the sorption of clay crystallites on cell-cell and cell-ECM complexes validate the concept of using these crystallites to enhance adhesion and are substantiated by the increased adhesive forces observed in the laboratory.

Example 1

Simulations Study

The inputs for a molecular simulation scheme include the choice of the representative molecules/crystallites, formulation of the representative unit cells with periodic boundary conditions, and the application of a force field to run the appropriate ensemble. The inventors' work includes the creation of cell-cell and cell-ECM configurations in molecular simulation software followed by the sorption and simulations of smectite clay crystallites with varying cation exchange capacity ("CEC") on the formulated configurations. The molecular simulations were carried out using Monte Carlo (MC) and molecular dynamics (MD) techniques using Materials Studio software; incorporated by reference to Accelrys Software (2013). *Materials Studio v7.0*: Accelrys Software Inc. California USA. Due to the large volume of computations involved in the simulations, these calculations were carried out at the high-performance computing facilities ("HPC") at KFUPM, KSA. Cohesive energy density ("CED"), considered as a measurement of the cohesiveness of the molecular system was determined for all the simulated configurations.

Selection and formulation of clay crystallites. Unit molecules used in the formulation are Na-montmorillonite crystallites of three different CECs. To study the relative effect of CEC on the simulation behavior, Na-montmorillonite molecules of three different CECs of 54, 90 and 144 meq/100 g were used. For the purpose of identification, these molecules were respectively named as Low CEC ("LCEC"), Medium CEC ("MCEC"), and High CEC ("HCEC"). Their charges were verified using the charge equilibration method QEq of the software.

For the clay minerals, all molecular level processes and interactions take place among the smallest particle size termed as fundamental crystal size or crystallite. The selection of dimensions of smallest or fundamental crystal/crystallite size is an important step in the molecular level modeling studies. The literature contains several studies about the determination of the fundamental crystal size of the clay minerals; see the following documents which are each incorporated by reference: Sucha V, Karus I, Samajova E and Puskelova L. *Crystallite size distribution of kaolin minerals*. International Journal of Mineralogy, Crystallography, Geochemistry, Ore Deposits, Petrology, Volcanology and applied topics on Environment, Archaeometry and Cultural Heritage 1999; 68: 81-92; Jonas E C and Oliver R M. *Size and Shape of Montmorillonite Crystallites*. Clays and Clay Minerals: Proceedings of the Fifteenth Conference, Pittsburgh, Pennsylvania, Clay Minerals Society, S. W. Oxford 1967; 27-33; Arnott R J. *Particle sizes of clay minerals by small-angle x-ray scattering*. The American Mineralogist 195; 50: 1563-1575; Simic V and Uhlik P. *Crystallite size distribution of clay minerals from selected Serbian clay deposits*. Annales Geologiques De La Peninsule Balkanique, Belgrade December 2006; 67: 109-116; and Uhlik P, Sucha V, Eberl D D, Puskelova L and Caplovicova M. *Evolution of pyrophyllite particle sizes during dry grinding*. Clay Minerals 2000; 35: 423-432.

Most of these studies have used XRD data and the physical imaging techniques such as Scanning and Transmission Electron Microscopy (SEM & TEM). In the inventors' work, the smallest molecular/crystallite size is selected as described by Ahmed H R and Abduljauwad S N. *Nanolevel constitutive model for expansive clays*. Geotechnique 2016; DOI; [http://_dx.doi.org/10.1680/jgeot.15.P.140]; and Ahmed H R. *Molecular level modeling of natural and compacted expansive clays*. Ph.D. Dissertation 2015, Civil Engineering Department, King Fahd University of Petroleum & Minerals (KFUPM), Saudi Arabia, both incorporated by reference.

In the inventors' work, the smallest crystallite size was determined by the analysis of the XRD data using the Scherrer method as described by Scherrer P. *Bestimmung der Grösse und der inneren Struktur von Kolloidteilchen mittels Röntgenstrahlen*. Nachr Ges Wiss Göttingen 1918; 26: 98-100, and by the relevant literature such as Simic V and Uhlik P. *Crystallite size distribution of clay minerals from selected Serbian clay deposits*. Annales Geologiques De La Peninsule Balkanique, Belgrade December 2006; 67: 109-116. Use of Scherrer method resulted in an approximate range of crystallites from 29 to 58 Å (2.9 to 5.8 nm). Simic and Uhlik determined crystallite size of the smectite of sedimentary origin using Bertaut-Warren-Averbach (BWA) technique. The crystallite size of smectite varied from about 2.0 to 10.0 nm with the maximum occurrence of about 2.41 nm and the mean values ranging from 5.21 to 5.79 nm. Similarly, for the sedimentary environments clay minerals precipitate as small particles (<10 nm) and grow in diameter over time as water provides a continuous supply of clay crystallites or sometimes referred to as 'building blocks' of the structure; see Eberl D D, Drits V A and Srodon J. *Deducing growth mechanisms for minerals from the shapes of crystal size distributions*. American Journal of Science 1998; 298: 499-533.

Using TEM data, it was also demonstrated that the <0.1 pm fractions of montmorillonite and regularly interstratified I-S consist of elementary particles 10 Å and 20 Å thick, respectively; see Nadeau P H, Tait J M, McHardy W J and Wilson M J. *Interstratified XRD characteristics of physical mixtures of elementary clay particles*. Clay Minerals 1984; 19: 67-76.

Figure 2:
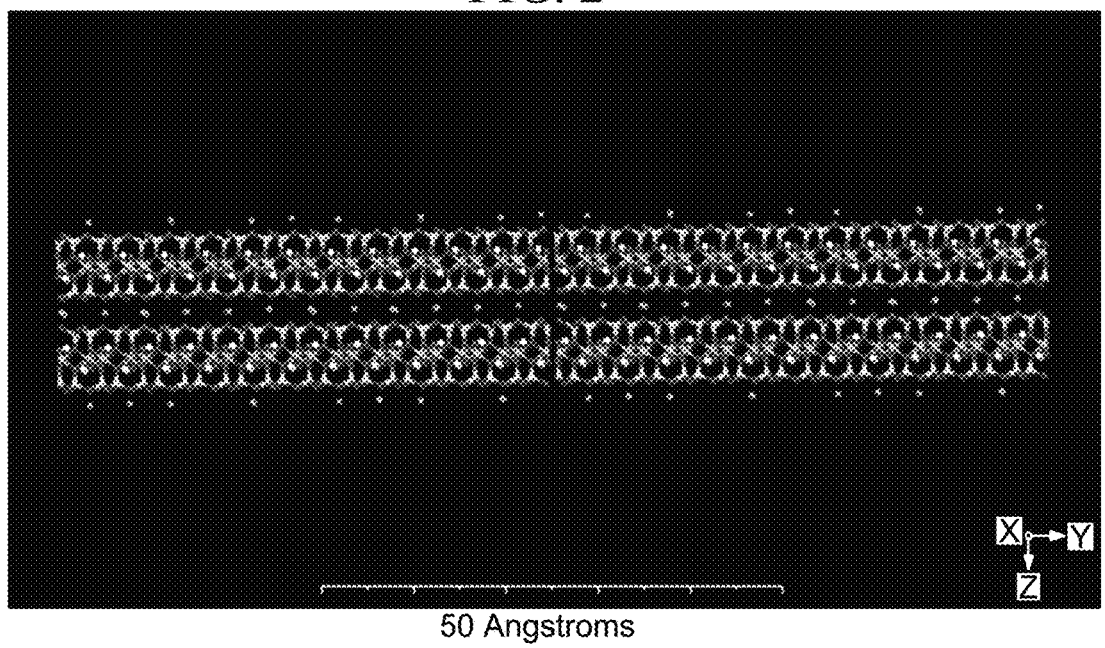
FIG. 2. Unit crystallite of Na-montmorillonite (26×108×20 Å) with CEC of 90 meq/100 g and sodium as an exchangeable cation. Scale bar=50 A.

Based on already published values and the XRD findings obtained in the inventors' research the fundamental crystallite size of 26×108×20 Å was chosen for the simulation as the fundamental particle/crystallite for Na-montmorillonite. A typical Na-montmorillonite model with a CEC of 90 meq/100 g and Na as the interlayer cation are shown in FIG. 2; see Ahmed H R and Abduljauwad S N. *Nanolevel constitutive model for expansive clays*. Geotechnique 2016; DOI; [http://_dx.doi.org/10.1680/jgeot.15.P.140]; and Ahmed H R. Molecular level modeling of natural and compacted expansive clays. Ph.D. Dissertation 2015, Civil Engineering Department, King Fahd University of Petroleum & Minerals (KFUPM), Saudi Arabia; both incorporated by reference.

Formulation of cell-ECM and cell-cell configurations. For the construction of the theoretical molecular level cell-ECM and cell-cell configurations, molecules of integrin, cadherin, and other associated ECM proteins such as laminins, collagen, and fibronectin were mainly acquired from protein data bank websites RCSB; Xiong J P, Stehle T, Diefenbach B, Zhang R, Dunker R, Scott D, Joachimiak A, Goodman S L and Arnaout M A. *Crystal Structure of the Extracellular Segment of Integrin AlphaVbeta3*. 2001. RCSB (2016) http://_www.rcsb.org/pdb/explore/) and PDB-101; and Shattil S J, Kim C and Ginsberg M H, *The final steps of integrin activation: the end game*. Nature Reviews Cell and Molecular Biology 11, 2011: 288-300. PDB-101 (2016) http://_pdb101.rcsb.org/. Also, plasma membrane files in protein data bank (PDB) format were acquired from University of Calgary website; *Lipid bilayers:* 128 *POPC lipids and* 2460 *water molecules.* University of Calgary (2016) http://_people.ucalgary.ca/~tieleman/download.html.

The integrin was created using three different parts formulating an inactive integrin. The top structure of the integrin that makes the extracellular portion extending outward from the cell surface (PDB entry 1jv2) was connected through the membrane by a short transmembrane section (PDB entry 2k9j) and the two short cytoplasmic tails extend into the cell (PDB entry 1m8o). Similarly, cadherin, in the form of large proteins that extend from the surface of the cell, were obtained from PDB entry 1l3w.

Figure 3:
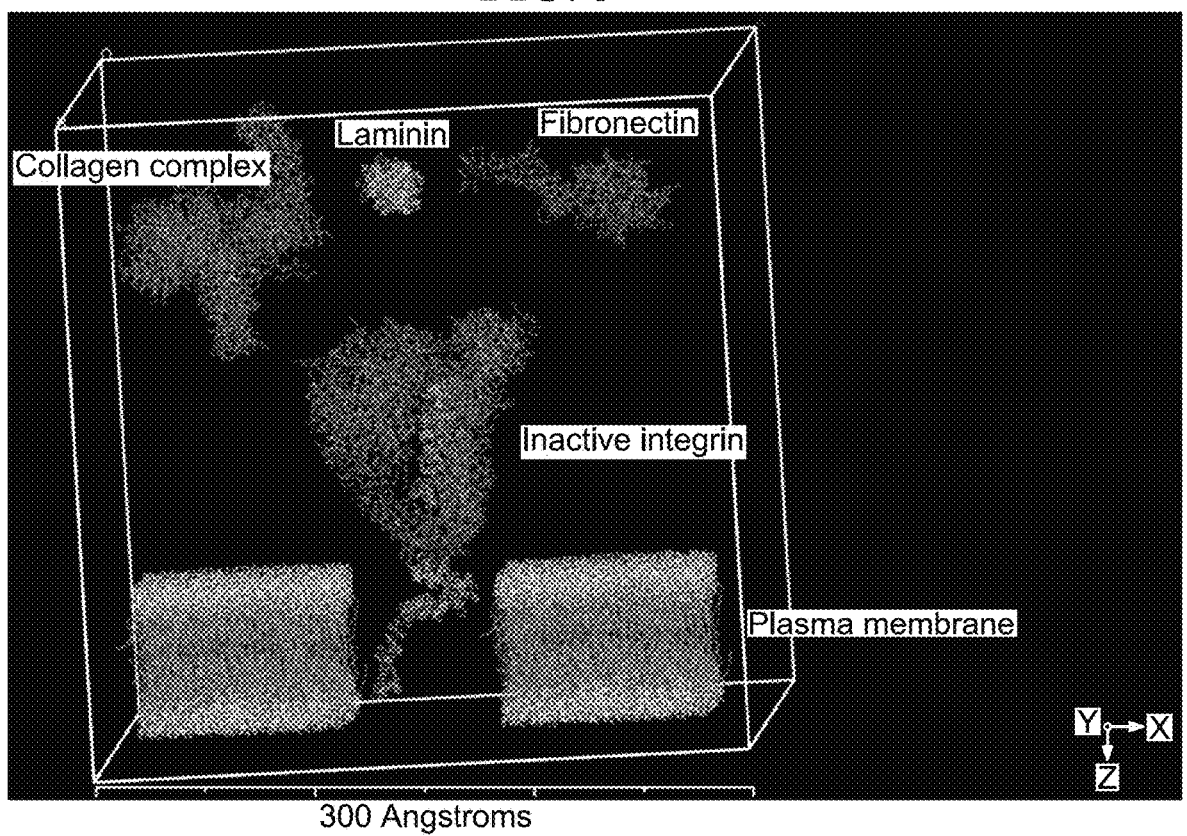
FIG. 3. A cell-ECM complex with an integrin, plasma membrane, and ECM proteins created in Materials Studio software. Scale bar=300 A.
Figure 4:
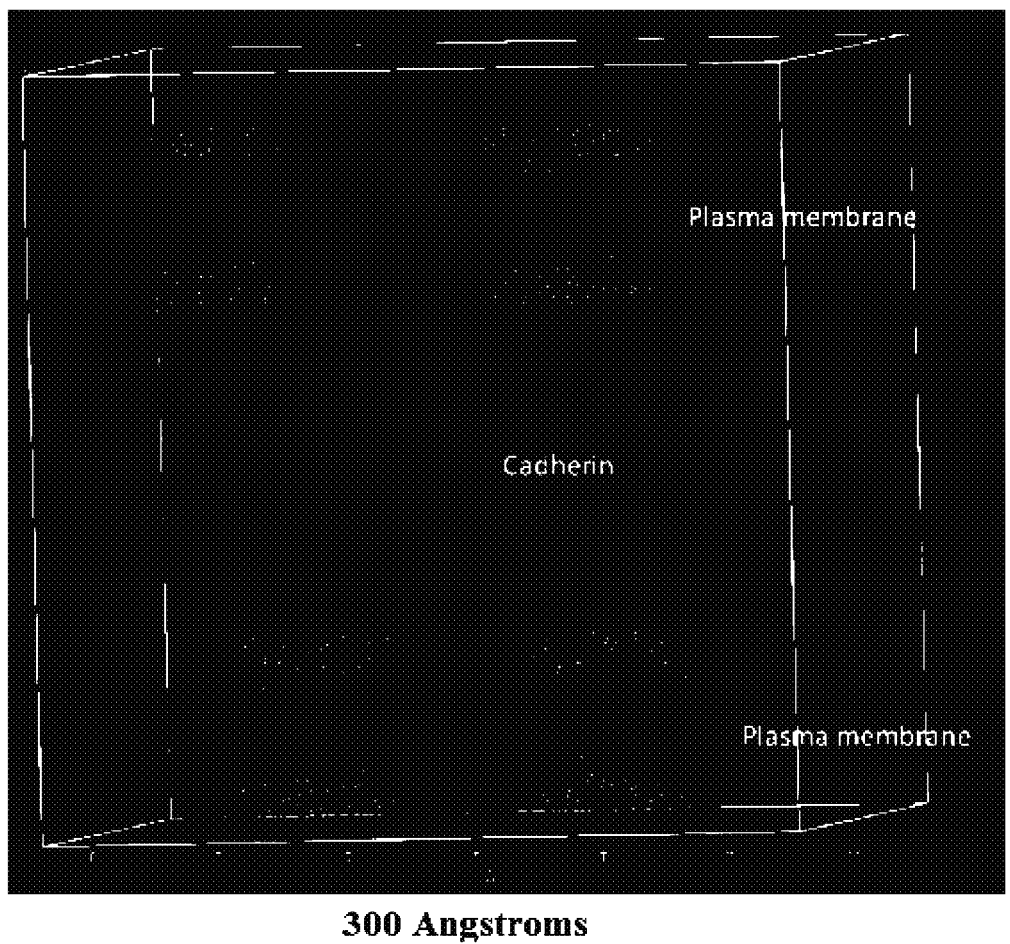
FIG. 4. A cell-cell complex with a cadherin connecting plasma membrane created in Materials Studio software. Scale bar=300 A.

For the formulation of cell-ECM configuration as shown by FIG. 3, the tail of the inactive integrin was sandwiched between two parts of the plasma membrane and the rest was kept protruding out towards ECM proteins. In this configuration, ECM was mimicked using three main proteins, i.e., collagen, laminins, and fibronectin. Similarly, cell-cell adhesion configuration was created using the ends of cadherin sandwiched between two parts of plasma membranes on both sides and the software generated unit cell is shown in FIG. 4. After placing the cell-cell and cell-ECM components within their relative positions and distances, the entire geometry was improved by lowering the energy using geometry option of Forcite module of the software.

Figure 5A:
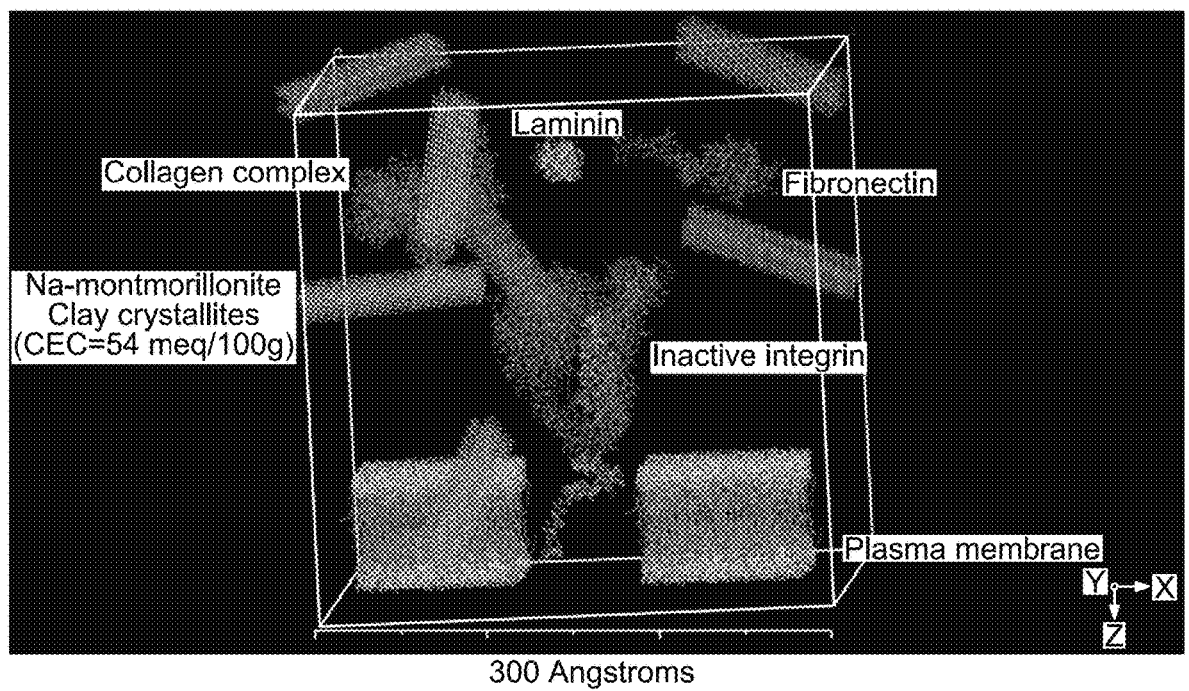
FIG. 5A. An integrin to plasma membrane and ECM proteins complex with sorbed LCEC (54 meq/100 g) crystallites.
Figure 5B:
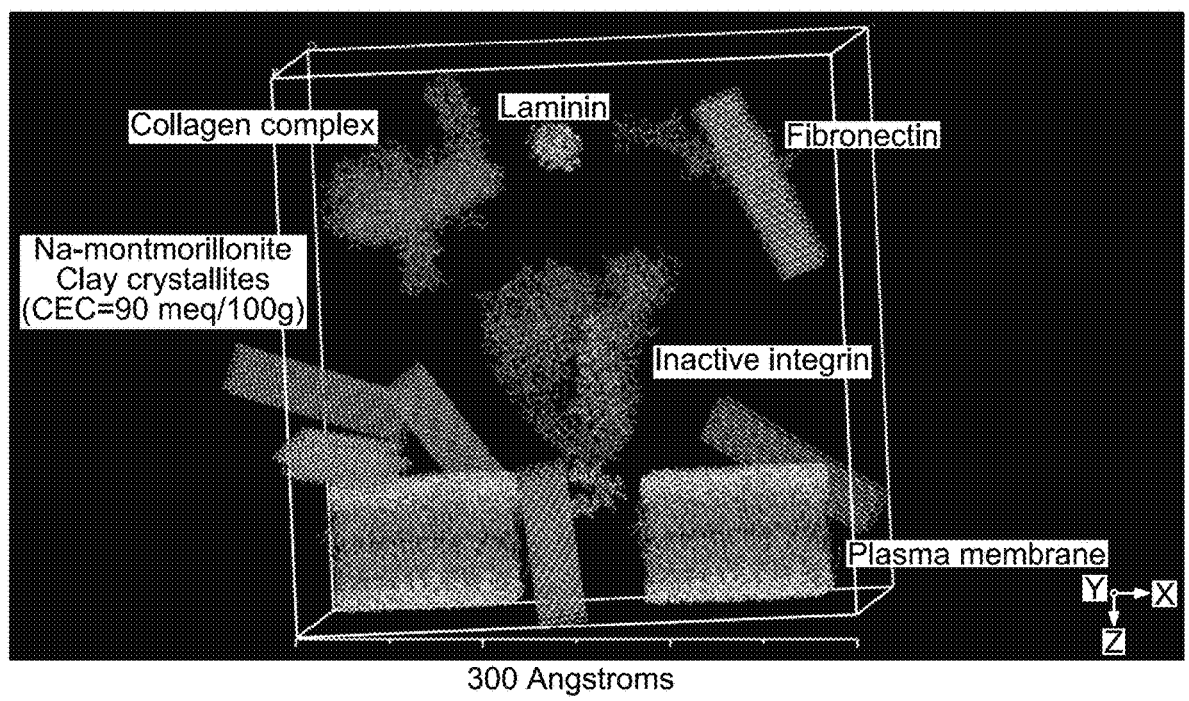
FIG. 5B. An integrin to plasma membrane and ECM proteins complex with sorbed MCEC (90 meq/100 g) crystallites.
Figure 5C:
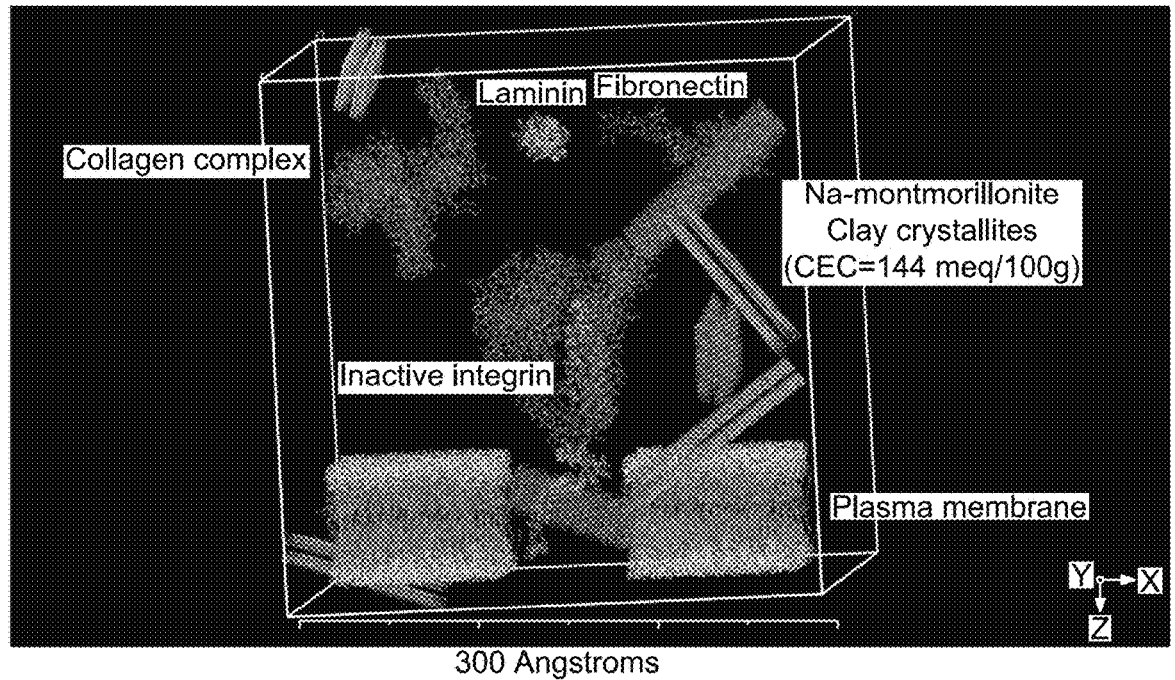
FIG. 5C. An integrin to plasma membrane and ECM proteins complex with sorbed HCEC (144 meq/100 g) crystallites. Scale bars=300 A.
Figure 6:
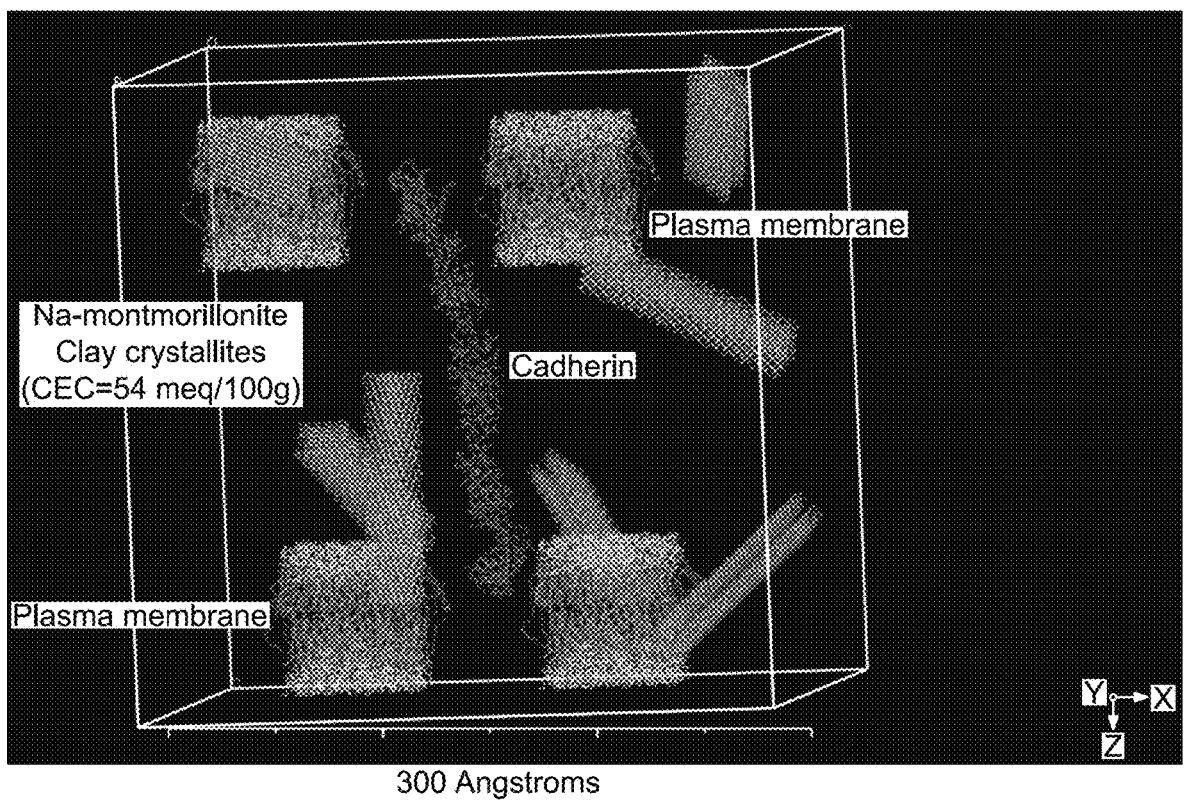
FIG. 6. A cadherin to plasma membrane complex with sorbed LCEC (54 meq/100 g) crystallites. Scale bar=300 A.

Na-montmorillonite crystallites interaction with cell-ECM and cell-cell configuration. To simulate the interaction of Na-montmorillonite crystallites with cell-cell and cell-ECM complexes, seven crystallites were sorbed on each configuration using Sorption module of the software. For the simulation purpose, Metropolis Monte Carlo method has been selected in the Sorption module of the software. In each sorption step, clay crystallites occupied spaces in the unit cell to lower the overall energy of the complex. Seven crystallites were sorbed in each 2,500 steps and then the energy of the system was minimized using Forcite module of the software based on Molecular Dynamics technique. The Forcite module of the Materials Studio software with the NPT (constant number of particles, pressure, and temperature) ensemble was used, and simulations were performed using a modified universal force field for 5 to 30 ps in 0.5-fs intervals or until a constant volume was reached. A Berendsen thermostat with a decay constant of 0.1 ps was used to control the temperature during the simulation. During the molecular-dynamics simulation, the assumed temperature was kept constant at 310° K (37° C.). Simulations were carried out assuming atmospheric pressure (100 kPa) and a Berendsen barostat with a decay constant of 0.1 ps was used to control the pressure of the system. The final configurations after sorbing LCEC, MCEC, and HCEC crystallites on the cell-ECM complex are shown in FIGS. 5A-5C respectively, while sorption of LCEC on cell-cell configuration is shown in FIG. 6.

The Berendsen methodology was selected as the most suitable for the single crystallites after several trials involving other thermostats and barostats available in the software. In Monte Carlo method, parameters chosen for ratios of exchange, conformer, rotate, translate, and regrow have been selected as 0.39, 0.2, 0.2, 0.2, 0.2 respectively, while the corresponding probabilities are 0.39, 0.2, 0.2, 0.2, and 0.2. Amplitudes adapted for rotation and translation are 5° and 1 Å respectively.

Electrostatic energy and cohesive energy density measurement. The effectiveness of clay crystallites to restore adhesions among cell-cell and cell-ECM complexes was evaluated through the changes in electrostatic attraction energies and cohesive energy densities. After the sorption of clay crystallites and the subsequent molecular dynamics of each of the configurations, energies were determined using Energy option of the Forcite module of the software. The Energy module provided total bond and non-bond energies of the configuration before and after the sorption of clay crystallites. Similarly, in this study cohesive energy density ('CED') concept very closely explained the various molecular-level processes and interactions and mimicked the extent of adhesion created among the simulated complexes. Quantitatively, CED is the amount of energy needed for the transition of 1 mol of material from the liquid to the gaseous phase and is considered as a measure of the mutual attractiveness of molecules. The CEDs of the simulated complexes were also determined using the Forcite module of the software. For comparison purposes, electrostatic energy and electrostatic CED were plotted against the CEC of the crystallites in FIG. 7.

Figure 7:
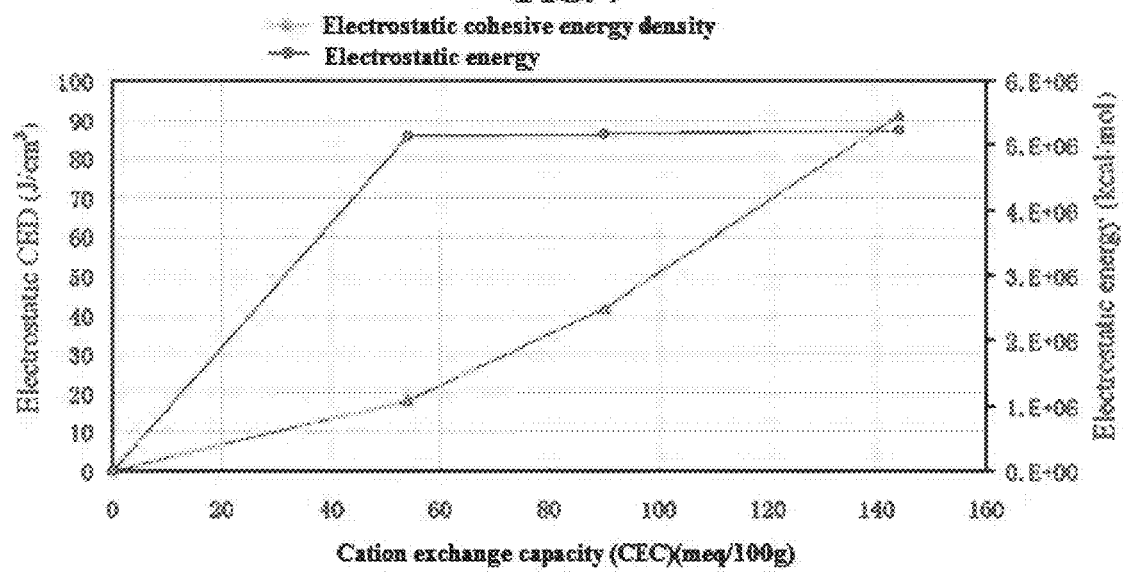
FIG. 7. Variation of electrostatic non-bond energy and an electrostatic component of cohesive energy density (CED) with CEC of the clay crystallites (zero on CEC axis represents the absence of clay).

Results and analysis of the molecular simulations. The sorbed Na-montmorillonite crystallites on cell-ECM and cell-cell configurations in FIGS. 5A-5C and 6 show that the crystallites, due to their charged nature, generally orient themselves with these configurations to provide an inter-connected network. This inter-connected network of crystallites results in the creation of an overall adhesiveness in the system. High electrostatic energies of an order of $5 \times 10^{-6}$ kcal/mol and electrostatic CEDs of up to 50-100 $J/cm^3$, shown in FIG. 7, are the evidence of the creation of adhesiveness in the complexes. It could also be noted from FIG. 7 that higher CEC clay crystallites have resulted in high level of adhesiveness. Therefore, for practical purposes, higher CEC clay would be preferred for the restoration of maximum adhesion among tumor or aging stem cells.

Based on the results of the inventors' work, clay crystallites are considered to exhibit properties that will restore adhesions in tumor and stem cells that have lost adhesiveness. Adhesion energies can be measured using bioforce probe (BFP), atomic force microscopy (AFM), and dual pipette assay (DPA) techniques. For the visualization of the interactions between clay crystallites and the cells, X-ray diffraction (XRD), environmental scanning electron microscopy (ESEM), and transmission electron microscopy (TEM) should be used.

Moreover, this study has demonstrated through molecular simulations the suitability of smectite (Na-montmorillonite) clay crystallites to create adhesions among tumor and stem cells. High electrostatic energies and cohesive energy densities measured in the simulations after the sorption of clay crystallites on cell-cell and cell-ECM complexes validate the concept of using these crystallites for the purposes such as restoring adhesiveness of tumor and stem cells.

Example 2

Restoration of Adhesion Among Tumor and Aging Stem Cells

Laboratory study. Laboratory testing involved the investigation of the effects of 3 types of nano-sized clay mineral particles on the adhesive properties of cancer and stem cells. The adhesion measurements included cell-extracellular matrix proteins in untreated and clay treated formulation. The adhesion among cancer and stem cells before and after the clay particles treatment were performed using Atomic Force Microscopy (AFM) at the laboratories of Miller School of Medicine, University of Miami, Florida Prior to adhesion tests, tests to determine the cytotoxicity effects, if any, of these clay particles on the cancer cells were also conducted.

Clay samples and preparation. To study the effect of clay minerals with different properties including cation exchange capacity (CEC), surface charges etc., three different types of clay minerals samples were selected for the adhesion studies. For the purpose, palygorskite (PFl-1), hectorite (SHCa-1), and Na-rich montmorillonite (SWy-3) were acquired from The Clay Minerals Society (2017), http://_www.clays.org/sourceclays_data.html.

The physical, chemical, and mineralogical properties of these clay samples are summarized in Table 1.

TABLE 1

Summary of chemical and physical characterization of clay samples

| Sample | Clay or mineral | Surface Area N2 (m2/g) | CEC (meq/100 g) | Exch. cations | Octahedral charge | Tetrahedral charge | Interlayer charge |
|---|---|---|---|---|---|---|---|
| PFI-1 | Palygorskite (Attapulgite) | 136.15 | 19.5 | — | −1.87 | −0.22 | −2.09 |
| SHCa-1 | Hectorite | 63.19 | 43.9 | — | −1.35 | −0.22 | −1.57 |
| SWy-3 | Na-Montmorillonite | 31.82 | 76.4 | Na, Ca | −0.53 | −0.02 | −0.55 |

During the initial trials, it was discovered that the clay particles in the mix at high concentration of 2 mg/ml could not be dissolved in the cell culture medium even when left overnight after mixing. For this purpose, the clays were made to go into solution by probe sonication technique at maximum power for about 20 minutes. Stock solutions (0.5 mg/ml) of the clay particles in Roswell Park Memorial Institute (RPMI) medium were prepared by sonicating the mixtures for 20 minutes to solubilize the clay particles. RPMI is a form of medium used in cell culture and tissue culture and contains a great deal of phosphate and is formulated for use in a 5% carbon dioxide atmosphere.

Cells and preparation. Raji, a human lymphoma cell line, were selected as model system representing the cancer cells. Lymphoma is the most common type of blood cancer. On the other hand, bone marrow-derived mesenchymal stem cells (MSCs) were used as a model system for stem cells.

Cytotoxicity verification. Before conducting the adhesion tests, it was required to verify the possible cytotoxicity of these clay particles on the cancer cells. For the purpose, the sterilized medium was required for the clay particles. To sterilize the medium for cell culture, the cleared clay solution of 0.2 mg/ml was autoclaved. The clay solutions were autoclaved for 30 min at 121° C. and at about 30 psi. The cancer cells were placed in the sterilized clay solution for one week to assess the cytotoxicity.

Crude cell adhesions. Before carrying out the adhesion measurements using AFM, a crude methodology was adopted to assess the feasibility of the tests. Crude cell adhesion assays were carried out on 96-well plates. The wells were either uncoated, coated with poly-L-lysine, or coated with fibronectin 24 hours prior to the assay. Raji cells, a lymphoma cell line, were labeled with a cell tracker dye and were added to the 96-well plate in standard medium or in medium containing one of three clay particles (0.1 mg/ml). Cells were returned to the incubator for 1 hr to allow cells to adhere. After 1 hr, loosely adherent cells were dislodged by dropping the inverted plate from a distance of approximately 20 cm from the lab bench. Although the actual cell dislodgement force can only be approximated is this assay, it is reasonable to assume that the cells in all of the wells of a given 96-well plate experienced the same dislodgement force. This then allows us to determine relative cell adhesion under the different condition by counting the number the cells that remained attached to the plate using a fluorescence plate reader. In the first experiment, SWy-3 clearly increased the adhesion of Raji cells to all 3 substrates (i.e., uncoated, poly-L-lysine, and fibronectin). With fibronectin-coated substrates, both SHCa-1 and SWy-3 increased adhesion. Interestingly, in the second assay, PFl-1 and SHCa-1 promoted adhesion, but SWy-3 did not. These crude cell adhesion assays helped to define conditions for the AFM force measurements.

Figure 8A:
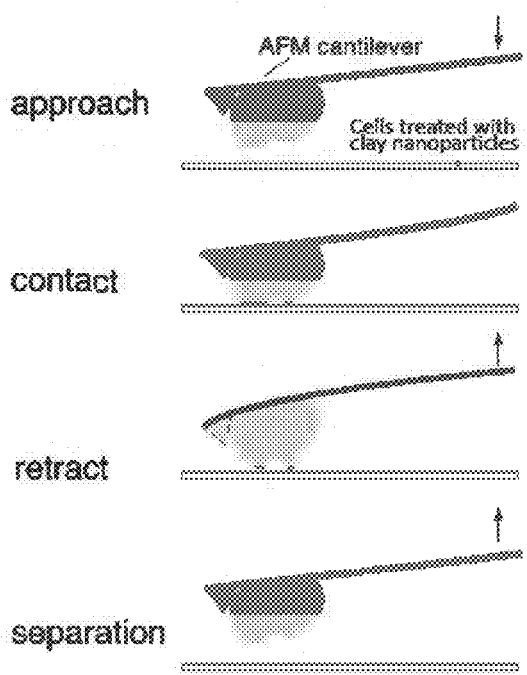
FIG. 8A. Schematic mechanism of adhesive force measurements using AFM. Principal events of AFM measurements: 1) Approach of the fibronectin to the cells treated with clay nanoparticles, 2) establishment of the contact, 3) retraction of fibronectin from the treated cells, and 4) its separation from the clay treated cells.

Measurements of cell adhesion by Atomic Force Microscopy (AFM). The metastatic properties of circulating tumor cells (CTC) have been attributed to the changes in cell-cell and cell-extracellular matrix adhesive interaction. The procedures for direct measurements of cell-extracellular matrix (ECM) adhesion were carried out by AFM. The AFM force measurements were carried out using a fibronectin-coated tipless cantilever (increased contact area) on an Asylum Research AFM. An experimental procedure has been developed to measure the mechanical force and work required to detach two interacting cells using the AFM. The technique is illustrated in FIG. 8A.

Figure 8B:
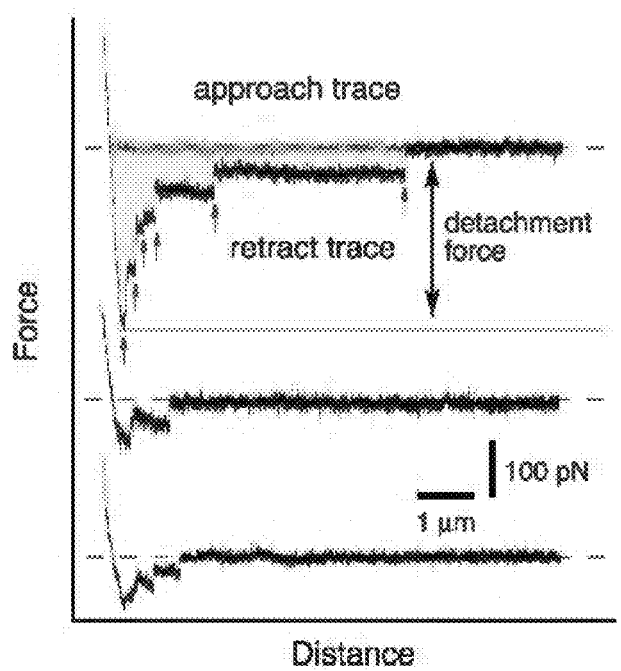
FIG. 8B. Typical force spectrum traces for fibronectin with cells.

To obtain a quantitative measure of the adhesion strength on a whole cell level, we used two adhesive indexes: 1) the detachment force and 2) the work of de-adhesion (FIG. 8B). Detachment force is the maximal adhesive force detected by the cantilever during cell-substrate separation. The work of de-adhesion, as indicated by the shaded area in the top trace of (FIG. 8B), is the work done by the cantilever to separate the cell and was derived from integrating the adhesive force over the distance traveled by the cantilever up to the point of the last bond rupture.

AFM measurements of cancer cell-ECM protein interaction. Measurements between fibronectin attached to the end of an AFM cantilever and a Raji monolayer plated on a tissue culture dish were carried out. A complete cycle of the AFM force scan is illustrated in FIG. 8A. The top trace of FIG. 8A represents a typical force curve of the interaction between fibronectins and Raji cells. The de-adhesion process involved multiple rupture events before finial separation. The middle trace in FIG. 8B recorded the interaction between Raji and fibronectin, which showed significant adhesion. Each test was repeated 3 times to ensure reproducibility.

For this assay, AFM cantilevers were functionalized with ECM proteins using a glutaraldehyde linkage. Cantilevers were initially salinized with 3-amino propyltriethoxysilane. After incubation of the cantilevers with 0.1% glutaraldehyde for 30 min, ECM proteins (2.5 μg/ml) were coupled to the cantilever through the glutaraldehyde linker. Incubation for 1 h with 1% bovine serum albumin (BSA) was used to block the bare surfaces of the cantilever.

Raji cells were immobilized on Petri dishes coated with poly-L-lysine. To determine the adhesive interaction between the captured cells and ECM protein functionalized cantilever, AFM force measurements were carried out as above for the cell-cell measurements and adhesion were quantified by the maximum force and work required to separate the cell from the functionalized cantilever.

AFM measurements of stem cell-ECM interaction. For this assay, AFM cantilevers were functionalized with ECM proteins using a glutaraldehyde linkage. Cantilevers were initially salinized with 3-aminopropyltriethoxysilane. After incubation of the cantilevers with 0.1% glutaraldehyde for 30 min, ECM proteins (2.5 µg/ml) were coupled to the cantilever through the glutaraldehyde linker. Incubation for 1 h with 1% bovine serum albumin (BSA) was used to block the bare surfaces of the cantilever.

To determine the adhesive interaction between the MSC cells and ECM protein functionalized cantilever, AFM force measurements were carried out as above for the cell-cell measurements and adhesion were quantified by the maximum force and work required to separate the cell from the functionalized cantilever.

Figure 9A:
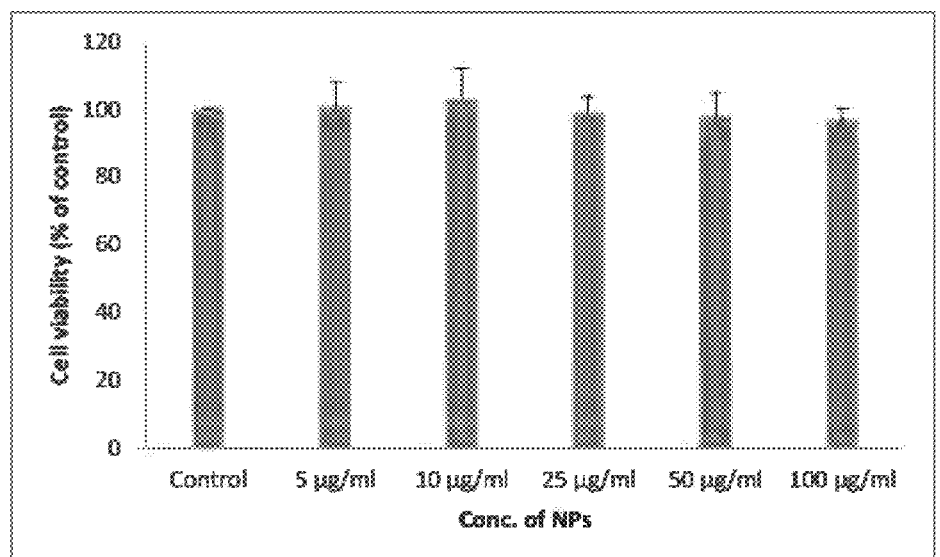
FIGS. 9A-9C, respectively: Trials 1, 2 and 3 of cytotoxicity analysis of the clay nanoparticles on breast cancer cells (MCF-7).
Figure 9B:
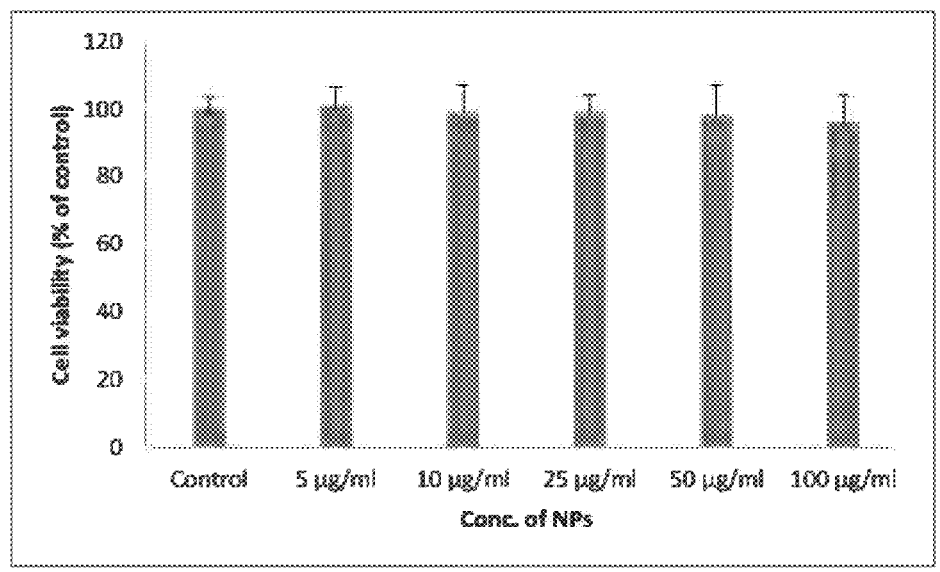
Figure 9C:
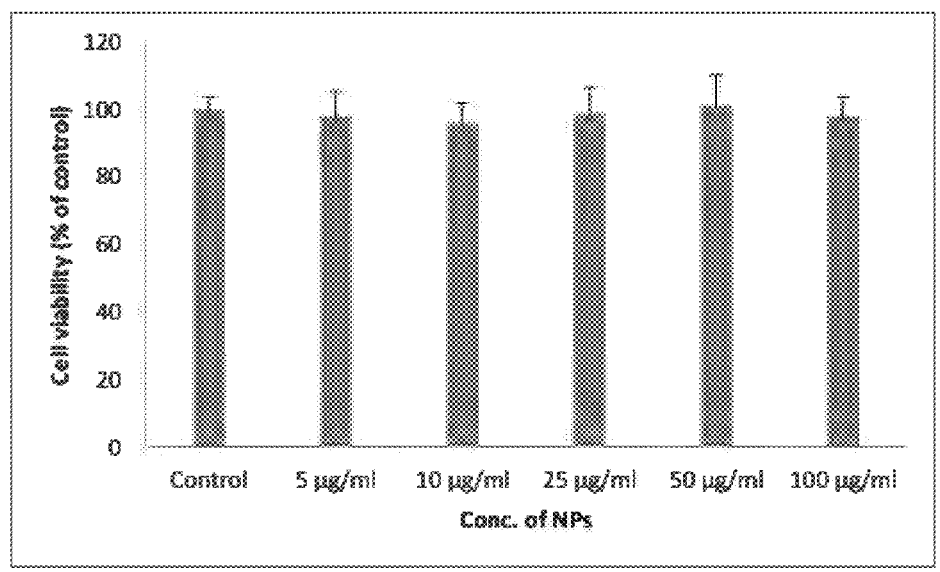

In Example 2, Raji cells, maintained in the medium saturated with clay did not appear to be toxic to the cells. The results shown in FIG. 9 showed no toxicity of the clay particles the cancer cells. As this study aimed at the use of the clay particles to enhance lost adhesion of the cancer and aging stem cells, lack of cytotoxicity of these clay particles were obvious and was not even targeted.

Figure 10A:
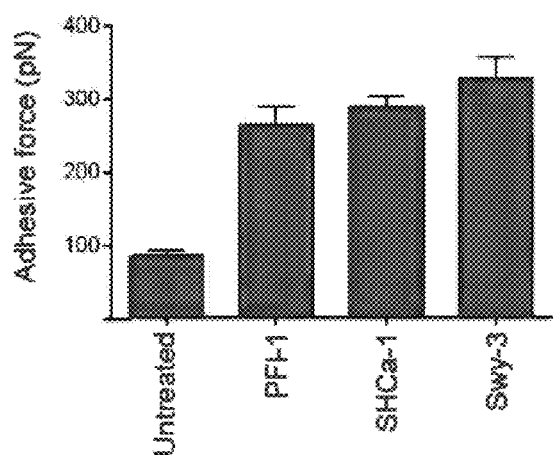
FIGS. 10A-10C, respectively: Trials 1, 2 and 3 of Adhesive force measurements among Raji cells and fibronectin protein of ECM before and after treatment with clay particles using AFM.
Figure 10B:
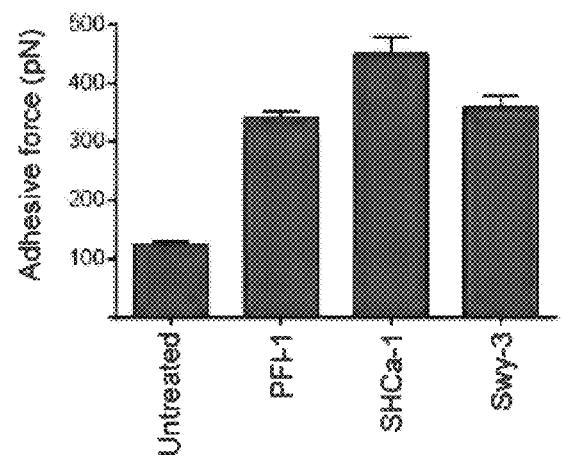
Figure 10C:
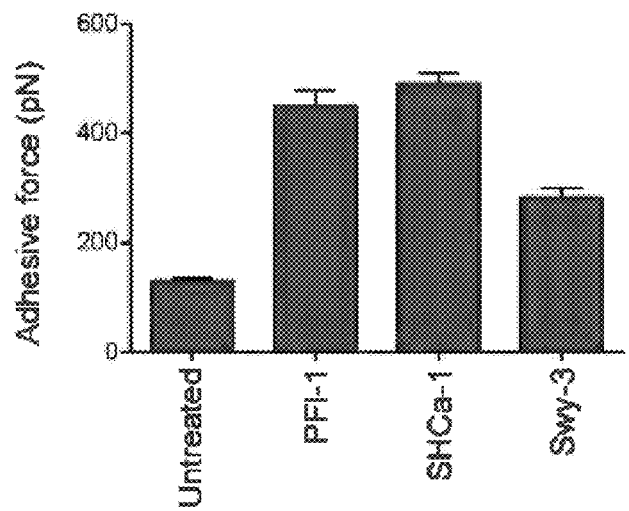
Figure 11A:
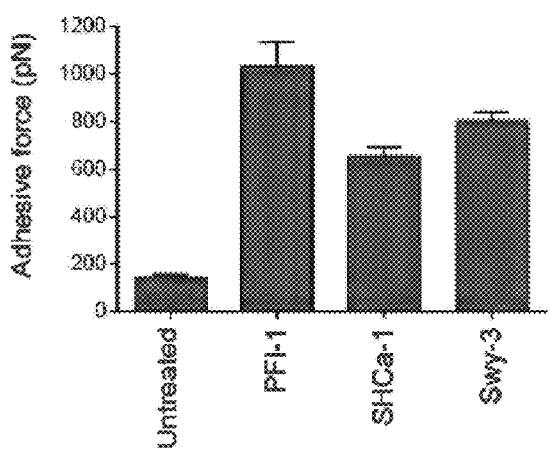
FIGS. 11A-11C, respectively: Trials 1, 2 and 3 of adhesive force measurements among MSC stem cells and fibronectin protein of ECM before and after treatment with clay particles using AFM.
Figure 11B:
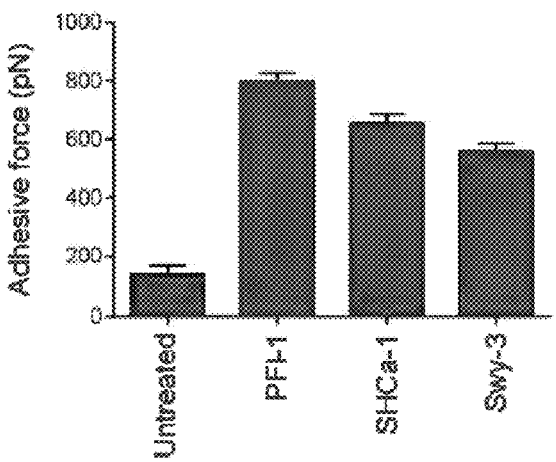
Figure 11C:
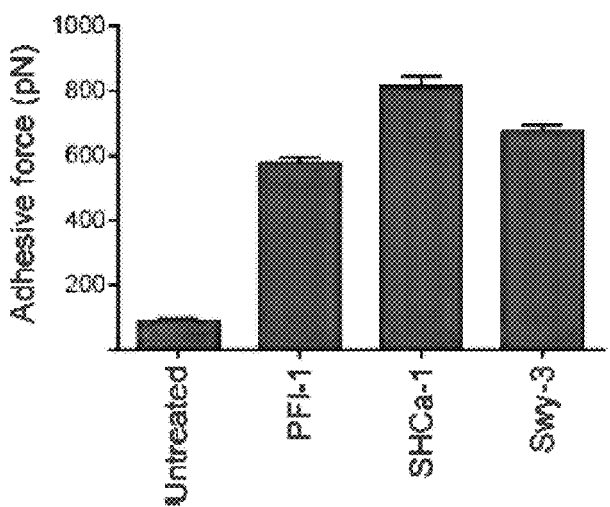

As evident from FIG. 10, there was a significant increase in adhesive force between the Raji cancer cells and fibronectin cantilever when any of the 3 clay particles (0.1 mg/ml) were present. Similarly, MSC stem cells have shown a considerable increase in the adhesion with fibronectin when treated with any of three types of clay; FIG. 11.

Figure 12:
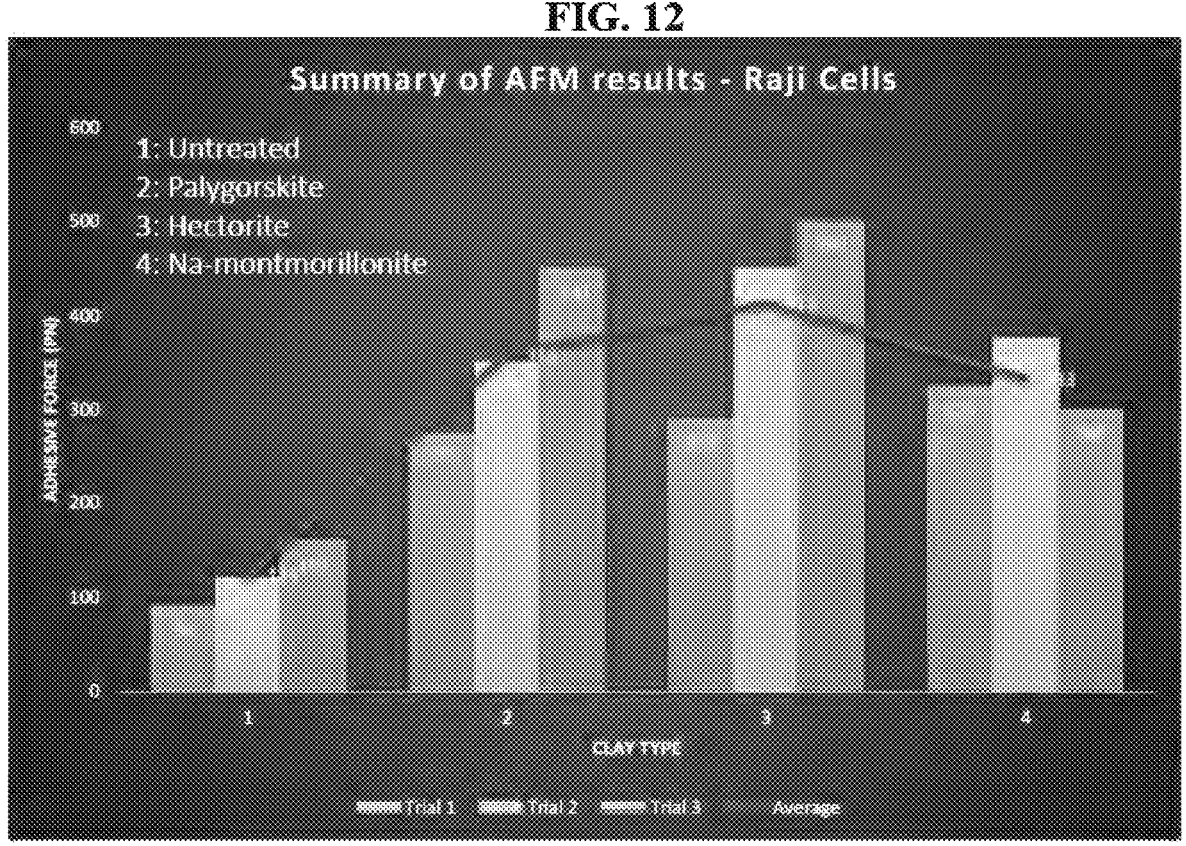
FIG. 12. Summary of adhesive force measurements among Raji cells and fibronectin before and after treatment with clay particles using AFM.
Figure 13:
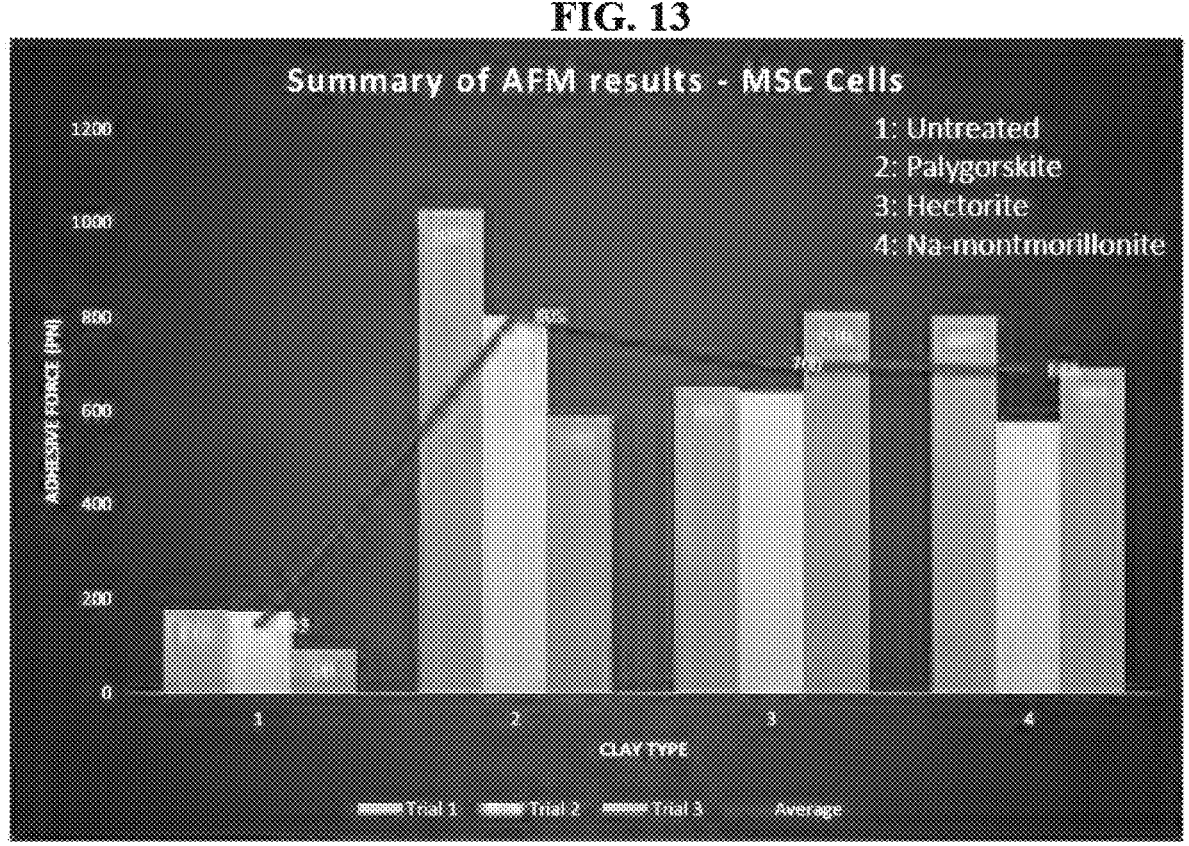
FIG. 13. Summary of adhesive force measurements among MSC stem cells and fibronectin before and after treatment with clay particles using AFM.

The adhesion tests results for Raji cells, summarized in FIG. 12, showed an increase in adhesion in the range of 170 to 236%. On average basis, Hectorite gave highest increase (236%) in adhesion while treatment with Na-montmorillonite resulted in lowest increase (170%) in the adhesion of the Raji cells with the ECM protein. Similarly, as shown by FIG. 13, there was a general increase in adhesion of MSC with ECM ranging from 374 to 455% when treatment different types of clays. In case of MSC-ECM interactions, Palygorskite gave the maximum increase of 455% while Na-montmorillonite resulted in relatively lesser increase in adhesion of 374%.

The experimental results acquired through AFM confirmed the results obtained using molecular level simulations by the authors; see Ahmed, H. R. and Abduljauwad, S. N. (2016), *Use of nano-sized clay crystallites to restore adhesion among tumor and aging stem cells—a molecular simulations approach*, Am J Stem Cells 2016; 5(4):107-115. These results show that due to substantial increase in adhesion among cancer cells, clay nanoparticles can be effectively used for the control of metastasis in cancer. Similarly these results are consistent with the capacity of treatment with clay or smectite nanoparticles to restore adhesion among stem cells, for example, for differentiation into various types of bone cells.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method of increasing cell adhesion, comprising:
preparing a composition by:
mixing nanosized smectite and saline;
wherein the composition consists of saline and nanosized smectite, and contacting Raji cells with the composition,
wherein the nanosized smectite is hectorite crystallites having a particle size of 50-100 nm and a cation exchange capacity (CEC) value of about 44 meq/100 g,
wherein the contacting results in an increase in adhesion force of the Raji cells to a target substrate of about 236%, compared to a same method but without contacting the Raji cells with the composition,
wherein the target substrate is an extracellular matrix (ECM) comprising fibronectin, and
wherein the adhesion force is measured between the fibronectin and the Raji cells by atomic force microscopy.

2. The method of claim 1, wherein the contacting comprises exposing the Raji cells to a concentration of 0.5 mg/ml of the nanosized smectite in the saline.

3. A method of increasing cell adhesion, comprising:
preparing a composition by:
mixing nanosized smectite and saline;
wherein the composition consists of saline and nanosized smectite, and contacting Raji cells with the composition,
wherein the nanosized smectite is palygorskite crystallites having a particle size of 30-75 nm and a cation exchange capacity (CEC) value of about 20 meq/100 g,
wherein the contacting results in an increase in adhesion force of the Raji cells to a target substrate of about 200%, compared to a same method but without contacting the Raji cells with the composition, wherein the target substrate is an extracellular matrix (ECM) comprising fibronectin, and wherein the adhesion force is measured between the fibronectin and the Raji cells by atomic force microscopy.

4. A method of increasing cell adhesion, comprising:
preparing a composition by:
  mixing nanosized smectite and saline;
  wherein the composition consists of saline and nanosized smectite, and contacting Raji cells with the composition,
wherein the nanosized smectite is Na-montmorillonite crystallites having a particle size of 55-100 nm and a CEC value of about 76 meq/100 g,
wherein the contacting results in an increase in adhesion force of the Raji cells to a target substrate of about 170%, compared to a same method but without contacting the Raji cells with the composition,
wherein the target substrate is an extracellular matrix (ECM) comprising fibronectin, and
wherein the adhesion force is measured between the fibronectin and the Raji cells by atomic force microscopy.

* * * * *